(12) United States Patent
Heinegard et al.

(10) Patent No.: US 7,211,649 B1
(45) Date of Patent: May 1, 2007

(54) CARTILAGE INTERMEDIATE LAYER PROTEIN

(75) Inventors: Dick Heinegard, Lund (SE); Pilar Lorenzo, Lund (SE)

(73) Assignee: Ana Mar Medical AB, Uppsala (SE)

( * ) Notice: Subject to any disclaimer, the term of this patent is extended or adjusted under 35 U.S.C. 154(b) by 340 days.

(21) Appl. No.: 10/349,188

(22) Filed: Jan. 23, 2003

Related U.S. Application Data

(60) Provisional application No. 60/142,054, filed on Jul. 2, 1999.

(51) Int. Cl.
*A61K 38/39* (2006.01)
*C07H 21/04* (2006.01)
*C12H 5/16* (2006.01)

(52) U.S. Cl. .................. 530/353; 536/23.5; 435/325

(58) Field of Classification Search ................ 530/350
See application file for complete search history.

(56) References Cited

U.S. PATENT DOCUMENTS

| | | | |
|---|---|---|---|
| 5,876,963 | A | 3/1999 | Mitchell et al. |
| 6,124,095 | A | 9/2000 | Magna et al. |

OTHER PUBLICATIONS

Attwood et al, The Babel of Bioinformatics, 2000, Science vol. 290 No. 5491: 471-473.*
Skolnick et al., From genes to protein structure and function: novel applications of computational approaches in the genomic era, Jan. 2000, Trends in Biotech. 18(1): 34-39.*
Kuby et al, 1994, Immunology, Second edition, pp. 85-96.*
Abaza et al., *J. Protein Chemistry* 11(5):433-444, 1992.
Lorenzo, P., et al., "A Novel Cartilage Protein (CLIP) Present in the Mid-zone of Human Articular Cartilage Increases with Age", *J. Biol. Chem.* 273(36):23463-23468, Sep. 4, 1998.
Lorenzo, P., et al., "Cloning and Deduced Amino Acid Sequence of a Novel Cartilage Protein (CLIP) Identifies a Proform Including a Nucleotide Pyrophosphohydrolase", *J. Biol. Chem.* 273(36):23469-23475, Sep. 4, 1998.
Lorenzo, P., et al., "The human CLIP gene: exon/intron organization and chromosomal mapping", *Matrix Biology* 18(5):455-454, Oct. 1999.
Marinescu, R. C., et al., "Exclusion of the Gene for Human Cartilage Intermediate Layer Protein in currently Mapped Calcium Pyrophosphate Dihydrate Deposition Syndromes", *Arthritis and Rheumatism* 42(10):2139-2144, Oct. 1999.
Masuda et al., *Gene* 197:277-287, 1997.
Nakamura, I., et al., "Genomic organization, mapping, and polymorphisms of the gene encoding human cartilage intermediate layer protein (CILP)", *J. Hum. Genet.* 44(3):203-205, 1999.
Ngo et al., "The Protein Folding Problem and Tertiary Structure Prediction", pp. 492-495, 1994.

* cited by examiner

*Primary Examiner*—Christina Chan
*Assistant Examiner*—Phuong Huynh
(74) *Attorney, Agent, or Firm*—Finnegan, Henderson, Farabow, Garrett & Dunner

(57) ABSTRACT

A novel, N-oligosaccharide-substituted-specific protein of approximately 91.5 kDa was purified from extracts of human articular cartilage and designated Cartilage Intermediate Layer Protein (CILP). The protein is a chondrocyte product which is deposited in the interterritorial matrix. The gene encoding CILP, as well as its mRNA, were isolated and characterized. A single 4.2 kb mRNA detected in human articular cartilage encodes a polypeptide of 1184 amino acids with a calculated molecular weight of 132.5 kDa. The protein has a putative signal peptide of 21 amino acids, and is a proform of two polypeptides. The amino-terminal half corresponds to CILP (molecular weight of 78.5 kDa, not including post-translational modifications) and the carboxy-terminal half corresponds to a protein homologous to a porcine nucleotide pyrophosphohydrolase, NTPPHase (molecular weight of 51.8 kDa, not including post-translational modifications).

9 Claims, 13 Drawing Sheets

```
GACCAGGAGACCCTCGCACGGCCAAGGAGATCGCGCTCGGCCGGTGCTTTGATGGCACATCCGATGGCTCCTCCAGAATCATGAAGAGCAATGGGAGTAGCCCTCACCTTCAACTGTGTA    3360
 D  Q  D  P  R  T  A  K  E  I  A  L  G  R  Ⓒ  F  D  G  T  S  D  G  S  S  R  I  M  K  S  N  V  G  V  A  L  T  F  N  Ⓒ  V     1099

GAGAGGCAAGTAGGCCGCCAGAGTGCCTTCCAGTACCTCCAAAGCACCCCCAGCCCCCAGTCCCTGCTGCAGGCACTGTCCAAGGAAGAGTGCCCTCGAGGAGGCAGCAGCGAGCGAGCAGG    3480
 E  R  Q  V  G  R  Q  S  A  F  Q  Y  L  Q  S  T  P  A  Q  S  P  A  A  G  T  V  Q  G  R  V  P  S  R  R  Q  Q  R  A  S  R     1139

GGTGGCCAGCGCCAGAGTGGAGTGGTGGCCTCTGAGATTTCCTAGAGTTGCTCAACAGCCCCTGATCAACTAAGTTTTGTGGTACTTCACCCCTCTCTGCCCTCATTTCATGTGACAG        3600
 G  G  Q  R  Q  S  G  V  V  A  S  L  R  F  P  P  R  V  A  Q  Q  P  L  I  N  ■  (SEQ ID NO:2)                                  1163

CCATTGTGAGACTGATGCACAAACTGTCACTTGGTTAATTTAAGCACTTCTGTTTGTTCTTCATGCCTTTACTTACTTGTCCATGCTACTGATTGGCAC                          3720
GTGGCCCCACAATGGCACAATAAAGCCCCTTTGTGAAACTGTTCTTTAAATGAACACAAGAAATTGGCCACTGGTAAAACTCTGCAGCTTCAACTGTACTTCATTTAATGCCATTAAT     3840
GCAAATATACTTCCTCTCTTTTTGCATGGTTTTGCCCACCTCTGCAATAGTGATAATCTGATGCTGAAGATCAATAAACCAATATAAGCATATTTCTTGGCCTTGCTCCACAGGACAT     3960
AGCCAAGCCTTGATCATAGTTCATACATATAAATGGTGTGAAATAAAGAGAATAAAACACAATACTTTTACTGGAAAAAAAAAAA      (SEQ ID NO:1)                    4046
```

FIG. 8C

SEQUENCE LISTING

<160> NUMBER OF SEQ ID NOS: 22

<210> SEQ ID NO 1
<211> LENGTH: 4175
<212> TYPE: DNA
<213> ORGANISM: Homo sapiens

<400> SEQUENCE: 1

```
tgaggagtcc tgctcaagac acggtcactg gatctgagaa acttcccagg ggaccgcatt      60
ccagagtcag tgactctgtg aagcacccac atctacctct tgccacgttc ccacgggctt     120
gggggaaaga tggtggggac caaggcctgg gtgttctcct tcctggtcct ggaagtcaca     180
tctgtgttgg ggagacagac gatgctcacc cagtcagtaa gaagagtcca gcctgggaag     240
aagaacccca gcatctttgc caagcctgcc gacaccctgg agagccctgg tgagtggaca     300
acattgttca acatcgacta cccaggcggg aagggcgact atgagcggct ggacgccatt     360
cgcttctact atgggaccg tgtatgtgcc cgtcccctgc ggctagaggc tcggaccact     420
gactggacac ctgcgggcag cactggccag gtggtccatg gtagtcccg tgagggtttc     480
tggtgcctca acagggagca gcggcctggc cagaactgct ctaattacac cgtacgcttc     540
ctctgcccac caggatccct gcgccgagac acagagcgca tctggagccc atggtctccc     600
tggagcaagt gctcagctgc ctgtggtcag actgggtcc agactcgcac acgcatttgc     660
ttggcagaga tggtgtcgct gtgcagtgag gccagcgaag agggtcagca ctgcatgggc     720
caggactgta cagcctgtga cctgacctgc ccaatggggc aggtgaatgc tgactgtgat     780
gcctgcatgt gccaggactt catgcttcat ggggctgtct cccttcccgg aggtgcccca     840
gcctcagggg ctgctatcta cctcctgacc aagacgccga agctgctgac ccagacagac     900
agtgatggga gattccgaat ccctggcttg tgccctgatg gcaaaagcat cctgaagatc     960
acaaaggtca agtttgcccc cattgtactc acaatgccca agactagcct gaaggcagcc    1020
accatcaagg cagagtttgt gagggcagag actccataca tggtgatgaa ccctgagaca    1080
aaagcacgga gagctgggca gagcgtgtct ctgtgctgta aggccacagg gaagcccagg    1140
ccagacaagt attttggta tcataatgac acattgctgg atccttccct ctacaagcat    1200
gagagcaagc tggtgctgag gaaactgcag cagcaccagg ctggggagta cttttgcaag    1260
gcccagagtg atgctgggtc tgtgaagtcc aaggttgccc agctgattgt cacagcatct    1320
gatgagactc cttgcaaccc agttcctgag agctatctta tccggctgcc ccatgattgc    1380
tttcagaatg ccaccaactc cttctactat gacgtgggac gctgccctgt taagacttgt    1440
gcagggcagc aggataatgg gatcaggtgc cgtgatgctg tgcagaactg ctgtggcatc    1500
tccaagacag aggaaaggga gatccagtgc agtggctaca gctacccac caaggtggcc    1560
aaggagtgca gctgccagcg gtgtacgaa actcggagca tcgtgcgggg ccgtgtcagt    1620
gctgctgaca atggggagcc catgcgcttt ggccatgtgt acatggggaa cagccgtgta    1680
agcatgactg gctacaaggg cactttcacc ctccatgtcc cccaggacac tgagaggctg    1740
gtgctcacat ttgtggacag gctgcagaag tttgtcaaca ccaccaaagt gctacctttc    1800
aacaagaagg ggagtgccgt gttccatgaa atcaagatgc ttcgtcggaa agagcccatc    1860
```

```
actttggaag ccatggagac caacatcatc cccctgggggg aagtggttgg tgaagacccc   1920
atggctgaac tggagattcc atccaggagt ttctacaggc agaatgggga gccctacata   1980
ggaaaagtga aggccagtgt gaccttcctg gatccccgga atatttccac agccacagct   2040
gcccagactg acctgaactt catcaatgac gaaggagaca ctttcccccct tcggacgtat   2100 ggcatgttct ctgtggactt cagagatgag gtcacctcag agccacttaa tgctggcaaa   2160
gtgaaggtcc accttgactc gacccaggtc aagatgccag agcacatatc cacagtgaaa   2220
ctctggtcac tcaatccaga cacagggctg tgggaggagg aaggtgattt caaatttgaa   2280
aatcaaagga ggaacaaaag agaagacaga accttcctgg tgggcaacct ggagattcgt   2340
gagaggaggc tctttaacct ggatgttcct gaaagcaggc ggtgctttgt taaggtgagg   2400
gcctaccgga gtgagaggtt cttgcctagt gagcagatcc aggggttgt gatctccgtg   2460 attaacctgg agcctagaac tggcttcttg tccaaccta gggcctgggg ccgctttgac   2520
agtgtcatca caggccccaa cggggcctgt gtgcctgcct tctgtgatga ccagtcccct   2580
gatgcctact ctgcctatgt cttggcaagc ctggctgggg aggaactgca agcagtggag   2640
tcttctccta aattcaaccc aaatgcaatt ggcgtccctc agccctatct caacaagctc   2700
aactaccgtc ggacggacca tgaggatcca cgggttaaaa agacagcttt ccagattagc   2760
atggccaagc caaggcccaa ctcagctgag gagagcaatg ggcccatcta tgcctttgag   2820
aacctccggg catgtgaaga ggcaccaccc agtgcagccc acttccggtt ctaccagatt   2880 gaggggatc gatatgacta caacacagtc cccttcaacg aagatgaccc tatgagctgg   2940
actgaagact atctggcatg gtggccaaag ccgatggaat tcagggcctg ctatatcaag   3000
gtgaagattg tggggccact ggaagtgaat gtgcgatccc gcaacatggg gggcactcat   3060
cggcggacag tggggaagct gtatggaatc cgagatgtga ggagcactcg ggacagggac   3120
cagcccaatg tctcagctgc ctgtctggag ttcaagtgca gtgggatgct ctatgatcag   3180
gaccgtgtgg accgcaccct ggtgaaggtc atccccccagg gcagctgccg tcgagccagt   3240
gtgaacccca tgctgcatga gtacctggtc aaccacttgc cacttgcagt caacaacgac   3300
accagtgagt acaccatgct ggcacccttg gacccactgg gccacaacta tggcatctac   3360
actgtcactg accaggaccc tcgcacggcc aaggagatcg cgctcggccg gtgctttgat   3420
ggcacatccg atggctcctc cagaatcatg aagagcaatg tgggagtagc cctcaccttc   3480
aactgtgtag agaggcaagt aggccgccag agtgccttcc agtacctcca aagcacccca   3540
gcccagtccc ctgctgcagg cactgtccaa ggaagagtgc cctcgaggag gcagcagcga   3600
gcgagcaggg gtgccagcg ccagagtgga gtggtggcct ctctgagatt tcctagagtt   3660
gctcaacagc ccctgatcaa ctaagttttg tggtacttca ccctcttctg ccctcatttc   3720
atgtgacagc cattgtgaga ctgatgcaca aactgtcact tggttaattt aagcacttct   3780
gttttcgtga atttgcttgt ttgtttcttc atgcctttac ttactttgtc ccatgctact   3840
gattggcacg tggcccccac aatggcacaa taaagcccct ttgtgaaact gttctttaaa   3900
tgaaacacaa gaaattggcc actggtaaaa ctctgcagct tcaactgtac ttcatttaat   3960
gccattaatg caaatatact tcctcttctt tttgcatggt tttgcccacc tctgcaatag   4020
tgataatctg atgctgaaga tcaaataacc aatataaagc atatttcttg gccttgctcc   4080
acaggacata ggcaagcctt gatcatagtt catacatata aatggtggtg aaataaagaa   4140
ataaaacaca atacttttac tggaaaaaaa aaaa                               4175
```

-continued

```
<210> SEQ ID NO 2
<211> LENGTH: 1184
<212> TYPE: PRT
<213> ORGANISM: Homo sapiens

<400> SEQUENCE: 2

Met Val Gly Thr Lys Ala Trp Val Phe Ser Phe Leu Val Leu Glu Val
  1               5                  10                  15

Thr Ser Val Leu Gly Arg Gln Thr Met Leu Thr Gln Ser Val Arg Arg
             20                  25                  30

Val Gln Pro Gly Lys Lys Asn Pro Ser Ile Phe Ala Lys Pro Ala Asp
         35                  40                  45

Thr Leu Glu Ser Pro Gly Glu Trp Thr Thr Leu Phe Asn Ile Asp Tyr
     50                  55                  60

Pro Gly Gly Lys Gly Asp Tyr Glu Arg Leu Asp Ala Ile Arg Phe Tyr
 65                  70                  75                  80

Tyr Gly Asp Arg Val Cys Ala Arg Pro Leu Arg Leu Glu Ala Arg Thr
                 85                  90                  95

Thr Asp Trp Thr Pro Ala Gly Ser Thr Gly Gln Val Val His Gly Ser
            100                 105                 110

Pro Arg Glu Gly Phe Trp Cys Leu Asn Arg Glu Gln Arg Pro Gly Gln
        115                 120                 125

Asn Cys Ser Asn Tyr Thr Val Arg Phe Leu Cys Pro Pro Gly Ser Leu
    130                 135                 140

Arg Arg Asp Thr Glu Arg Ile Trp Ser Pro Trp Ser Pro Trp Ser Lys
145                 150                 155                 160

Cys Ser Ala Ala Cys Gly Gln Thr Gly Val Gln Thr Arg Thr Arg Ile
                165                 170                 175

Cys Leu Ala Glu Met Val Ser Leu Cys Ser Glu Ala Ser Glu Glu Gly
            180                 185                 190

Gln His Cys Met Gly Gln Asp Cys Thr Ala Cys Asp Leu Thr Cys Pro
        195                 200                 205

Met Gly Gln Val Asn Ala Asp Cys Asp Ala Cys Met Cys Gln Asp Phe
    210                 215                 220

Met Leu His Gly Ala Val Ser Leu Pro Gly Gly Ala Pro Ala Ser Gly
225                 230                 235                 240

Ala Ala Ile Tyr Leu Leu Thr Lys Thr Pro Lys Leu Leu Thr Gln Thr
                245                 250                 255

Asp Ser Asp Gly Arg Phe Arg Ile Pro Gly Leu Cys Pro Asp Gly Lys
            260                 265                 270

Ser Ile Leu Lys Ile Thr Lys Val Lys Phe Ala Pro Ile Val Leu Thr
        275                 280                 285

Met Pro Lys Thr Ser Leu Lys Ala Thr Ile Lys Ala Glu Phe Val
    290                 295                 300

Arg Ala Glu Thr Pro Tyr Met Val Met Asn Pro Glu Thr Lys Ala Arg
305                 310                 315                 320

Arg Ala Gly Gln Ser Val Ser Leu Cys Cys Lys Ala Thr Gly Lys Pro
                325                 330                 335

Arg Pro Asp Lys Tyr Phe Trp Tyr His Asn Asp Thr Leu Leu Asp Pro
            340                 345                 350

Ser Leu Tyr Lys His Glu Ser Lys Leu Val Leu Arg Lys Leu Gln Gln
        355                 360                 365

His Gln Ala Gly Glu Tyr Phe Cys Lys Ala Gln Ser Asp Ala Gly Ala
    370                 375                 380
```

-continued

```
Val Lys Ser Lys Val Ala Gln Leu Ile Val Thr Ala Ser Asp Glu Thr
385                 390                 395                 400

Pro Cys Asn Pro Val Pro Glu Ser Tyr Leu Ile Arg Leu Pro His Asp
            405                 410                 415

Cys Phe Gln Asn Ala Thr Asn Ser Phe Tyr Tyr Asp Val Gly Arg Cys
                420                 425                 430

Pro Val Lys Thr Cys Ala Gly Gln Gln Asp Asn Gly Ile Arg Cys Arg
            435                 440                 445

Asp Ala Val Gln Asn Cys Cys Gly Ile Ser Lys Thr Glu Glu Arg Glu
    450                 455                 460

Ile Gln Cys Ser Gly Tyr Thr Leu Pro Thr Lys Val Ala Lys Glu Cys
465                 470                 475                 480

Ser Cys Gln Arg Cys Thr Glu Thr Arg Ser Ile Val Arg Gly Arg Val
            485                 490                 495

Ser Ala Ala Asp Asn Gly Glu Pro Met Arg Phe Gly His Val Tyr Met
            500                 505                 510

Gly Asn Ser Arg Val Ser Met Thr Gly Tyr Lys Gly Thr Phe Thr Leu
        515                 520                 525

His Val Pro Gln Asp Thr Glu Arg Leu Val Leu Thr Phe Val Asp Arg
    530                 535                 540

Leu Gln Lys Phe Val Asn Thr Thr Lys Val Leu Pro Phe Asn Lys Lys
545                 550                 555                 560

Gly Ser Ala Val Phe His Glu Ile Lys Met Leu Arg Arg Lys Glu Pro
                565                 570                 575

Ile Thr Leu Glu Ala Met Glu Thr Asn Ile Ile Pro Leu Gly Glu Val
            580                 585                 590

Val Gly Glu Asp Pro Met Ala Glu Leu Glu Ile Pro Ser Arg Ser Phe
        595                 600                 605

Tyr Arg Gln Asn Gly Glu Pro Tyr Ile Gly Lys Val Lys Ala Ser Val
        610                 615                 620

Thr Phe Leu Asp Pro Arg Asn Ile Ser Thr Ala Thr Ala Ala Gln Thr
625                 630                 635                 640

Asp Leu Asn Phe Ile Asn Asp Glu Gly Asp Thr Phe Pro Leu Arg Thr
                645                 650                 655

Tyr Gly Met Phe Ser Val Asp Phe Arg Asp Glu Val Thr Ser Glu Pro
            660                 665                 670

Leu Asn Ala Gly Lys Val Lys Val His Leu Asp Ser Thr Gln Val Lys
        675                 680                 685

Met Pro Glu His Ile Ser Thr Val Lys Leu Trp Ser Leu Asn Pro Asp
690                 695                 700

Thr Gly Leu Trp Glu Glu Gly Asp Phe Lys Phe Glu Asn Gln Arg
705                 710                 715                 720

Arg Asn Lys Arg Glu Asp Arg Thr Phe Leu Val Gly Asn Leu Glu Ile
            725                 730                 735

Arg Glu Arg Arg Leu Phe Asn Leu Asp Val Pro Glu Ser Arg Arg Cys
        740                 745                 750

Phe Val Lys Val Arg Ala Tyr Arg Ser Glu Arg Phe Leu Pro Ser Glu
        755                 760                 765

Gln Ile Gln Gly Val Val Ser Val Ile Asn Leu Glu Pro Arg Thr
770                 775                 780

Gly Phe Leu Ser Asn Pro Arg Ala Trp Gly Arg Phe Asp Ser Val Ile
785                 790                 795                 800
```

```
Thr Gly Pro Asn Gly Ala Cys Val Pro Ala Phe Cys Asp Asp Gln Ser
            805                 810                 815

Pro Asp Ala Tyr Ser Ala Tyr Val Leu Ala Ser Leu Ala Gly Glu Glu
            820                 825                 830

Leu Gln Ala Val Glu Ser Ser Pro Lys Phe Asn Pro Asn Ala Ile Gly
            835                 840                 845

Val Pro Gln Pro Tyr Leu Asn Lys Leu Asn Tyr Arg Arg Thr Asp His
850                 855                 860

Glu Asp Pro Arg Val Lys Lys Thr Ala Phe Gln Ile Ser Met Ala Lys
865                 870                 875                 880

Pro Arg Pro Asn Ser Ala Glu Glu Ser Asn Gly Pro Ile Tyr Ala Phe
            885                 890                 895

Glu Asn Leu Arg Ala Cys Glu Glu Ala Pro Ser Ala His Phe
            900                 905                 910

Arg Phe Tyr Gln Ile Glu Gly Asp Arg Tyr Asp Tyr Asn Thr Val Pro
            915                 920                 925

Phe Asn Glu Asp Asp Pro Met Ser Trp Thr Glu Asp Tyr Leu Ala Trp
930                 935                 940

Trp Pro Lys Pro Met Glu Phe Arg Ala Cys Tyr Ile Lys Val Lys Ile
945                 950                 955                 960

Val Gly Pro Leu Glu Val Asn Val Arg Ser Arg Asn Met Gly Gly Thr
            965                 970                 975

His Arg Arg Thr Val Gly Lys Leu Tyr Gly Ile Arg Asp Val Arg Ser
            980                 985                 990

Thr Arg Asp Arg Asp Gln Pro Asn Val Ser Ala Ala Cys Leu Glu Phe
            995                 1000                1005

Lys Cys Ser Gly Met Leu Tyr Asp Gln Asp Arg Val Asp Arg Thr Leu
    1010                1015                1020

Val Lys Val Ile Pro Gln Gly Ser Cys Arg Arg Ala Ser Val Asn Pro
1025                1030                1035                1040

Met Leu His Glu Tyr Leu Val Asn His Leu Pro Leu Ala Val Asn Asn
                1045                1050                1055

Asp Thr Ser Glu Tyr Thr Met Leu Ala Pro Leu Asp Pro Leu Gly His
            1060                1065                1070

Asn Tyr Gly Ile Tyr Thr Val Thr Asp Gln Asp Pro Arg Thr Ala Lys
    1075                1080                1085

Glu Ile Ala Leu Gly Arg Cys Phe Asp Gly Thr Ser Asp Gly Ser Ser
    1090                1095                1100

Arg Ile Met Lys Ser Asn Val Gly Val Ala Leu Thr Phe Asn Cys Val
1105                1110                1115                1120

Glu Arg Gln Val Gly Arg Gln Ser Ala Phe Gln Tyr Leu Gln Ser Thr
            1125                1130                1135

Pro Ala Gln Ser Pro Ala Ala Gly Thr Val Gln Gly Arg Val Pro Ser
            1140                1145                1150

Arg Arg Gln Gln Arg Ala Ser Arg Gly Gly Arg Gln Ser Gly Val
            1155                1160                1165

Val Ala Ser Leu Arg Phe Pro Arg Val Ala Gln Gln Pro Leu Ile Asn
    1170                1175                1180

<210> SEQ ID NO 3
<211> LENGTH: 18
<212> TYPE: PRT
<213> ORGANISM: Homo sapiens

<400> SEQUENCE: 3
```

Glu Asp Arg Thr Phe Leu Val Gly Asn Leu Glu Ile Arg Glu Arg Arg
 1               5                  10                  15

Leu Phe

<210> SEQ ID NO 4
<211> LENGTH: 19
<212> TYPE: PRT
<213> ORGANISM: Homo sapiens
<220> FEATURE:
<221> NAME/KEY: UNSURE
<222> LOCATION: (18)
<223> OTHER INFORMATION: X AT POSITION 18 INDICATES UNIDENTIFIED RESIDUE

<400> SEQUENCE: 4

Ala Glu Phe Val Asp Ala Glu Thr Pro Tyr Met Val Met Asn Pro Glu
 1               5                  10                  15

Thr Xaa Lys

<210> SEQ ID NO 5
<211> LENGTH: 10
<212> TYPE: PRT
<213> ORGANISM: Homo sapiens

<400> SEQUENCE: 5

Phe Ala Pro Ile Val Leu Asp Met Pro Lys
 1               5                  10

<210> SEQ ID NO 6
<211> LENGTH: 7
<212> TYPE: PRT
<213> ORGANISM: Homo sapiens

<400> SEQUENCE: 6

Asn Pro Ser Ile Phe Ala Lys
 1               5

<210> SEQ ID NO 7
<211> LENGTH: 16
<212> TYPE: PRT
<213> ORGANISM: Homo sapiens
<220> FEATURE:
<221> NAME/KEY: UNSURE
<222> LOCATION: (6)
<223> OTHER INFORMATION: X AT POSITION 6 INDICATES UNIDENTIFIED RESIDUE

<400> SEQUENCE: 7

Tyr Phe Trp Tyr His Xaa Thr Thr Leu Leu Asp Pro Ser Leu Tyr Lys
 1               5                  10                  15

<210> SEQ ID NO 8
<211> LENGTH: 24
<212> TYPE: PRT
<213> ORGANISM: Homo sapiens

<400> SEQUENCE: 8

Gly Thr Phe Thr Leu His Val Pro Gln Asp Thr Glu Arg Leu Val Leu
 1               5                  10                  15

Thr Phe Val Asp Arg Leu Gln Lys
             20

<210> SEQ ID NO 9
<211> LENGTH: 13
<212> TYPE: PRT
<213> ORGANISM: Homo sapiens

```
<220> FEATURE:
<221> NAME/KEY: UNSURE
<222> LOCATION: (11)
<223> OTHER INFORMATION: X AT POSITION 11 INDICATES UNIDENTIFIED RESIDUE

<400> SEQUENCE: 9

Pro Ala Asp Thr Leu Glu Ser Pro Met Glu Xaa Thr Thr
 1               5                  10

<210> SEQ ID NO 10
<211> LENGTH: 21
<212> TYPE: PRT
<213> ORGANISM: Homo sapiens

<400> SEQUENCE: 10

Glu Pro Ile Thr Leu Glu Ala Met Glu Thr Asn Ile Ile Pro Leu Gly
 1               5                  10                  15

Glu Val Val Gly His
            20

<210> SEQ ID NO 11
<211> LENGTH: 16
<212> TYPE: PRT
<213> ORGANISM: Homo sapiens
<220> FEATURE:
<221> NAME/KEY: UNSURE
<222> LOCATION: (15)
<223> OTHER INFORMATION: X AT POSITION 15 INDICATES UNIDENTIFIED RESIDUE

<400> SEQUENCE: 11

Leu Trp Ser Leu Asn Pro Asp Thr Gly Leu Glu Glu Glu Gly Xaa Phe
 1               5                  10                  15

<210> SEQ ID NO 12
<211> LENGTH: 5
<212> TYPE: PRT
<213> ORGANISM: Homo sapiens

<400> SEQUENCE: 12

Leu Val Leu Arg Lys
 1               5

<210> SEQ ID NO 13
<211> LENGTH: 9
<212> TYPE: PRT
<213> ORGANISM: Homo sapiens

<400> SEQUENCE: 13

Ala Thr Gly Lys Pro Arg Pro Asp Lys
 1               5

<210> SEQ ID NO 14
<211> LENGTH: 17
<212> TYPE: PRT
<213> ORGANISM: Homo sapiens

<400> SEQUENCE: 14

Val His Leu Asp Ser Thr Gln Val Lys Met Pro His Ile Ser Thr Val
 1               5                  10                  15

Lys

<210> SEQ ID NO 15
<211> LENGTH: 7
<212> TYPE: PRT
<213> ORGANISM: Homo sapiens
```

```
<400> SEQUENCE: 15

Leu His Val Pro Gln Asp Thr
 1               5

<210> SEQ ID NO 16
<211> LENGTH: 6
<212> TYPE: PRT
<213> ORGANISM: Homo sapiens

<400> SEQUENCE: 16

Glu Ala Met Glu Thr Asn
 1               5

<210> SEQ ID NO 17
<211> LENGTH: 7
<212> TYPE: PRT
<213> ORGANISM: Homo sapiens

<400> SEQUENCE: 17

Pro Tyr Met Val Met Asn Pro
 1               5

<210> SEQ ID NO 18
<211> LENGTH: 25
<212> TYPE: DNA
<213> ORGANISM: Homo sapiens
<220> FEATURE:
<221> NAME/KEY: modified_base
<222> LOCATION: (19)
<223> OTHER INFORMATION: i - n AT POSITION 19 IS INOSINE

<400> SEQUENCE: 18
gtacaatggg ggcaaactng acctt                               25

<210> SEQ ID NO 19
<211> LENGTH: 25
<212> TYPE: DNA
<213> ORGANISM: Homo sapiens

<400> SEQUENCE: 19
tcatgaagag caatgtggga gtagc                               25

<210> SEQ ID NO 20
<211> LENGTH: 7
<212> TYPE: DNA
<213> ORGANISM: Homo sapiens
<220> FEATURE:
<221> NAME/KEY: variation
<222> LOCATION: (2)..(3)
<223> OTHER INFORMATION: n AT POSITIONS 2 AND 3 INDICATE ANY NUCLEOTIDE
<220> FEATURE:
<221> NAME/KEY: modified_base
<222> LOCATION: (5)
<223> OTHER INFORMATION: n AT POSITION 5 IS URACIL

<400> SEQUENCE: 20 rnnangg                                                    7

<210> SEQ ID NO 21
<211> LENGTH: 5
<212> TYPE: PRT
<213> ORGANISM: Homo sapiens

<400> SEQUENCE: 21

Trp Ser Pro Trp Ser
```

```
<210> SEQ ID NO 22
<211> LENGTH: 19
<212> TYPE: PRT
<213> ORGANISM: Homo sapiens

<400> SEQUENCE: 22

Glu Asp Arg Thr Phe Leu Val Gly Asn Leu Glu Ile Arg Glu Arg Arg
  1               5                  10                  15

Leu Phe Cys
```

CARTILAGE INTERMEDIATE LAYER PROTEIN

CROSS-REFERENCE TO RELATED APPLICATION

This application relies on, and claims the benefit of the filing date of, U.S. Provisional Application Ser. No. 60/142,054, filed Jul. 2, 1999, the entire disclosure of which is hereby incorporated herein by reference.

BACKGROUND OF THE INVENTION

1. Field of the Invention

The present invention relates to the field of molecular biology and protein biochemistry. More particularly, it relates to purification and characterization of proteins present in the matrix of cartilage-containing tissues, and to the cloning and characterization of genes encoding these proteins.

2. Description of the Related Art

Articular cartilage is a heterogeneous tissue in which cells are arranged in layers, forming a matrix. The layers have a different composition and function depending on their location with respect to the articular surface of the subchondral bone. The extracellular matrix is also arranged into compartments around the cells: pericellular (closest to the cell), territorial (extending around individual or groups of chondrocytes), and interterritorial matrix (farthest away from the cells). The matrix is produced by the chondrocytes and contains, as major constituents, fibril-forming DERSON, collagens and large aggregating proteoglycans that are assembled into highly organized structures (Heinegård, D. and Oldberg, Å., 1993, In Connective Tissue and Its Hereditable Disorders (Royce, P. M. and Steinmann, B., eds.) pp. 103–147, Wiley-Liss Inc., New York). Collagen confers tensile properties to the tissue, whereas proteoglycans play a key role in the normal resilience and load dissipation of the cartilage.

There is also a minor population of non-collagenous proteins for which no functional role has yet been identified. They might have roles in maintaining the tissue homeostasis by the regulation of matrix assembly, cell recognition, and cell attachment. They might also have a part to play in balancing the processes of cartilage repair and degradation, as well as in disease processes where degradation outbalances repair, and loss of tissue ensues. This third set of matrix proteins are the non-collagenous glycoproteins, including several members of the family of leucine-rich repeat (LRR) proteins and the thrombospondins. The LRR proteins include decorin, biglycan, fibromodulin, and lumican, all with the capacity to bind to collagen (for refs. see Heinegård et al., 1998, "Biochemistry and metabolism of normal and OA cartilage", In Osteoarthritis, K. D. Brant, M. Doherty, and S. Lohmander, eds., Oxford University Press, New York, In press). These molecules are found along surfaces of collagen fibrils in the tissue.

Other members of this family include chondroadherin (Neame et al., 1994, "The structure of a 38-kDa leucine-rich protein (Chondroaherin) isolated from bovine cartilage", *J. Biol. Chem.* 269:21547–21554) and PRELP (Bengtsson et al., 1995, "The primary structure of a basic leucine-rich repeat protein, PRELP, found in connective tissues", *J. Biol. Chem.* 270:25639–25644). The thrombospondin family includes the pentameric COMP, which is one of the more abundant cartilage matrix proteins (Hedbom et al., 1992, "Cartilage matrix proteins. An acidic oligomeric protein (COMP) detected only in cartilage", *J. Biol. Chem.* 267:6132–6136; Oldberg et al., 1992, "COMP (cartilage oligomeric matrix protein) is structurally related to thrombospondins", *J. Biol. Chem.* 267:22346–22350). Furthermore, thrombospondins-1 has been identified in articular cartilage (Miller and McDevitt, 1988, "Thrombospondin is present in articular cartilage and is synthesized by articular chondrocytes", *Biochem. Biophys. Res. Commun.* 153:708–714). There are also a number of other proteins that might not be part of the described families.

Interestingly, in joint disease, such as osteoarthrosis (OA; also known as osteoarthritis) there are major alterations in the composition of the cartilage extracellular matrix. These changes reflect an altered homeostasis, and might play a role in defective repair (Heinegård et al., supra).

Preliminary studies by the present inventors and their colleagues have shown that there are a set of proteins whose synthesis and content are increased in early OA cartilage. In most cases the structure and function of these proteins are not known. However, detailed knowledge of their structure, function, and variability in normal conditions, as well as in disease, is of fundamental importance in defining mechanisms and events occurring in joint disease. Thus, to identify matrix constituents involved in these processes, it is imperative to identify, isolate, and characterize these matrix proteins.

Osteoarthritis is a non-inflammatory bone disorder characterized by a slowly progressing matrix degeneration punctuated by short periods of inflammation. During the degeneration process, there is degradation of matrix molecules, including collagens and proteoglycans and subsequent release of matrix fragments into the synovial fluid. Loss of movement and strength, in the affected joints, often due to pain, are the predominant clinical manifestations of the disease. Pain killers are the most often prescribed treatment. Because osteoarthritis is a slowly progressing disease, it is desirable to detect the disease early in its development and treat it before extensive damage has occurred. There exists a need for methods and compositions for early detection of this clinically important disease. Possible markers for osteoarthritis, which could be used early in the development of the disease, include the matrix proteins.

SUMMARY OF THE INVENTION

One such matrix protein is the protein of the present invention. This protein, referred to herein as Cartilage Intermediate Layer Protein (CILP), has been identified and purified from human articular cartilage. The present invention describes the isolation and characterization of a CILP that is a 91.5 kDa, single-chain protein from human articular cartilage. The invention also describes methods of making CILP, portions (fragments) of CILP, and analogs and homologs of CILP.

Further, the present invention provides methods of using the proteins (and fragments) of the invention, including use in early detection of OA, treatment of individuals suffering from joint disease, such as OA, use in identifying other cartilage matrix proteins, and use in identifying the biochemical and biophysical bases of OA. An additional use of the protein or protein fragments of the invention is in the production of antibodies specific for the protein.

Thus, the present invention includes antibodies that specifically react with CILP, immunogenic fragments of CILP, and cross-reactive analogs and homologs of CILP. Using the antibodies of the present invention, other CILP-related proteins can be identified and isolated.

The present invention also provides nucleic acids encoding the protein of the invention, portions (fragments) of the protein, or analogs or homologs of the protein. In addition, the invention provides other nucleic acids encoding all or part of CILP, such as messenger RNA (mRNA) encoding all or part of CILP, as well as probes and primers for identifying, isolating, and characterizing other CILP proteins, analogs, and/or homologs. Having provided nucleic acids encoding the protein of the invention, or parts thereof, the invention also provides methods of isolating, or otherwise producing, the nucleic acids of the invention.

Methods of using the nucleic acids are also provided by this invention. Included in these methods are methods for producing the proteins of the invention, as well as methods of producing portions of the proteins, such as immunogenic portions. The nucleic acids of the invention can also be used in methods of treatment, such as therapeutic methods for treatment of OA. Methods of detecting, isolating, and purifying nucleic acids encoding analogous or homologous proteins are provided through the use of probes and primers according to the present invention. Methods of identifying genes involved in OA are enabled by the present invention, as are transgenic animals in which CILP expression is controlled or eliminated.

An additional aspect of the invention is a kit containing reagents necessary for making or using the protein of the invention, making or using the nucleic acid of the invention, or making and using the antibodies of the invention. For example, the nucleic acids of the invention can be supplied in a kit, for both in vivo and in vitro applications, or the antibodies of the invention can be supplied in a kit for detection of abnormal levels of CILP or immunoreactive fragments or analogs of CILP.

BRIEF DESCRIPTION OF THE DRAWINGS

The accompanying drawings, which are incorporated in, and constitute a part of, this specification, illustrate several embodiments of the invention and together with the description, serve to help explain the principles of specific embodiments of the invention.

A. 4–16% SDS PAGE gel (Coomassie-stained).

B. Immunoblot of the gel from A, using antiserum against the human CILP.

For both A and B, lane 1: purified CILP. Lane 2: extracts from human articular cartilage. Lane 3: extracts from cow articular cartilage. Lane 4: extracts from rat chondrosarcoma. Lane 5: extracts from dog articular cartilage. Lane 6: extracts from horse articular cartilage.

Figure 2B:
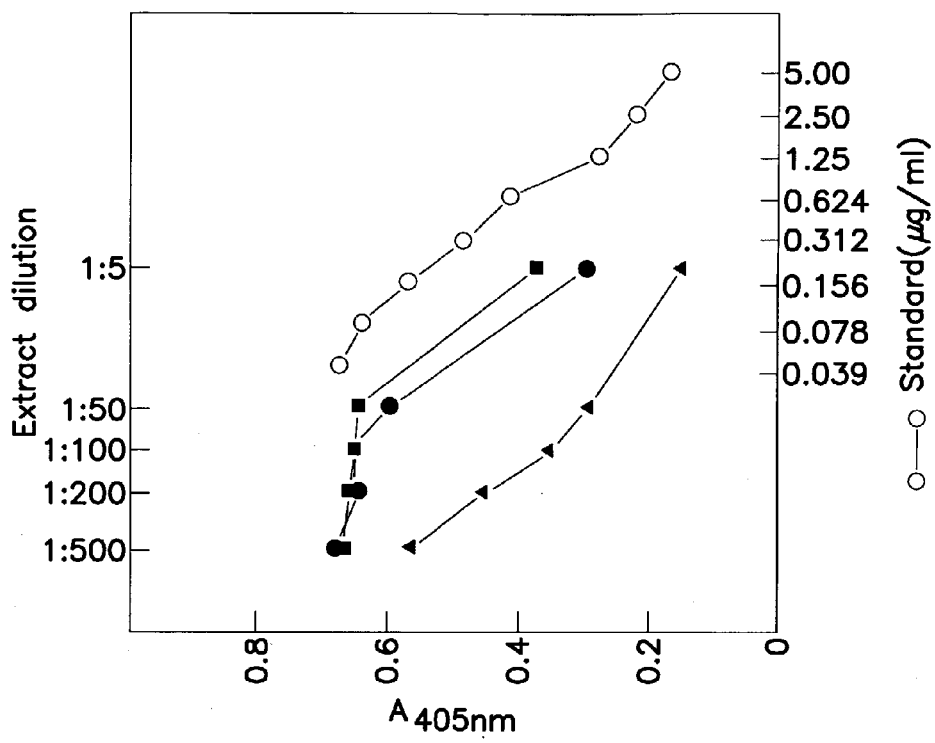
Figure 2A:
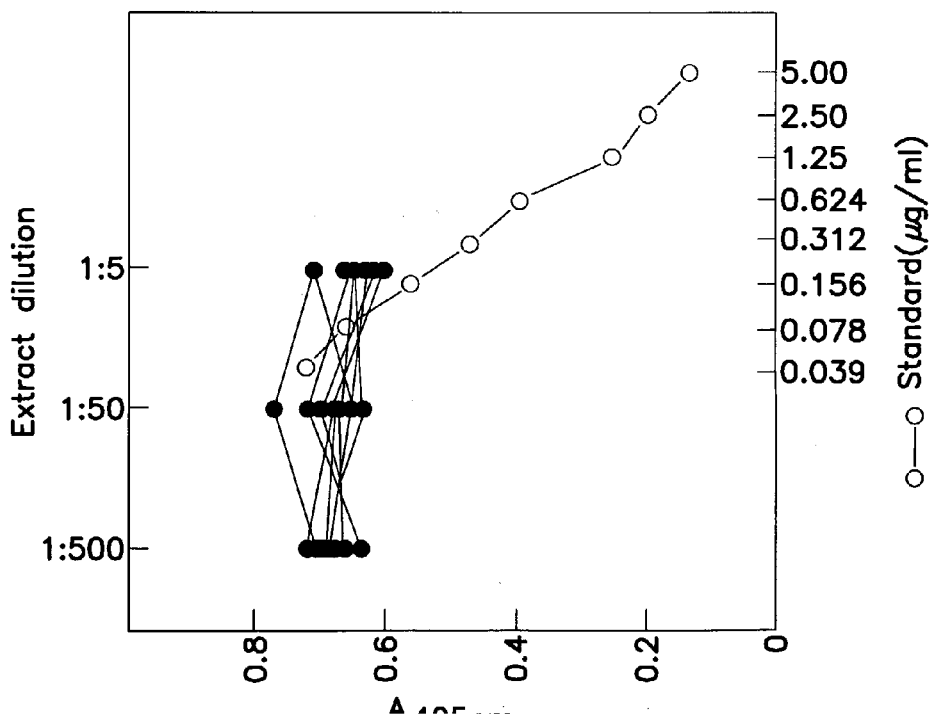

FIG. 2 shows the results of an ELISA of CILP in human tissues.

A. Non-cartilagenous tissues: liver, kidney, intestine, lung, skin, aorta, muscle, tendon, and bone (all represented by solid circles).

B. Cartilages: tracheal (■), articular (●), rib/costal (▲).

For both A and B, purified CILP is represented by open circles.

Figure 3:
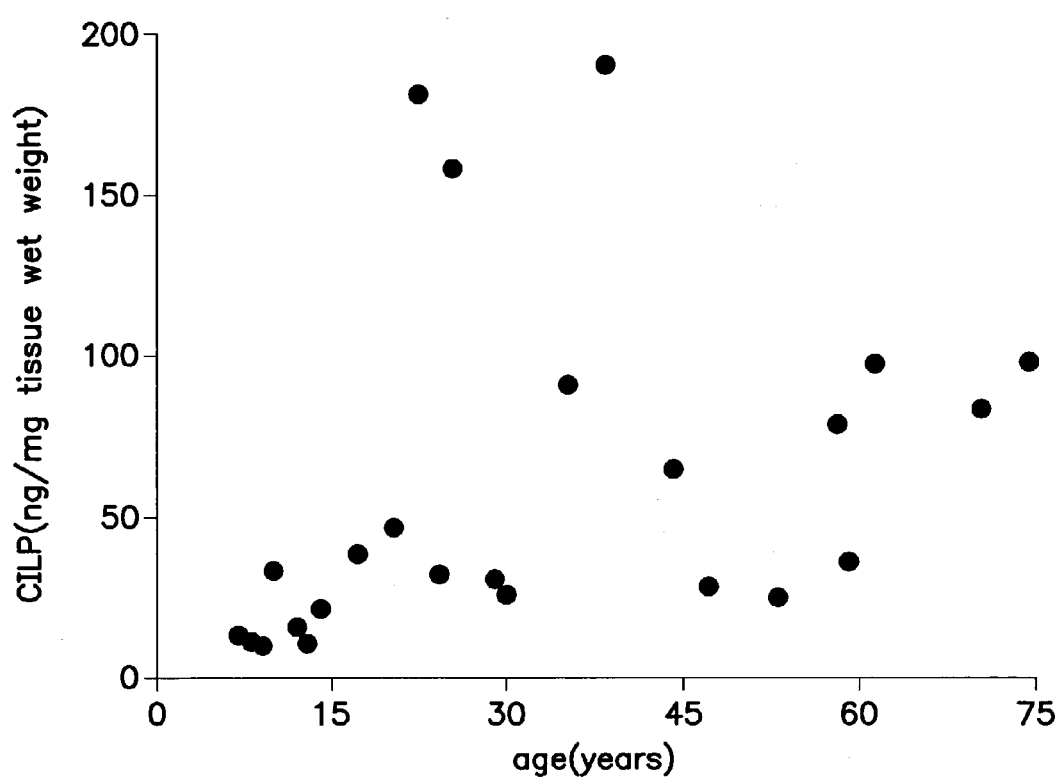

FIG. 3 shows CILP content in articular cartilages from individuals of different ages. All samples were analyzed in triplicate, and the mean value was used for calculations.

Figure 4A:
Figure 4B:
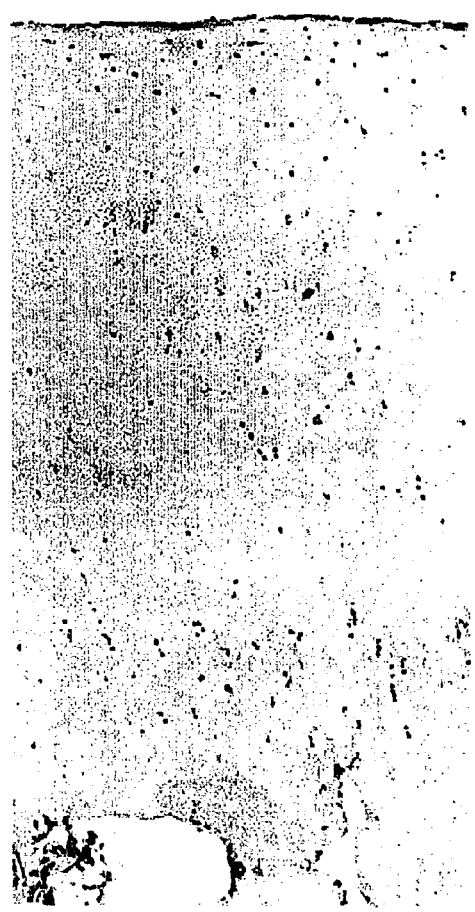

FIG. 4 shows the immunolocalization of CILP in human articular cartilage (hip). Polyclonal antibodies to CILP were used.

A. Sections were pre-digested with testicular hyaluronidase before incubation with anti-CILP antibodies.

B. Sections were pre-incubated with pre-immune sera.

Figure 5:
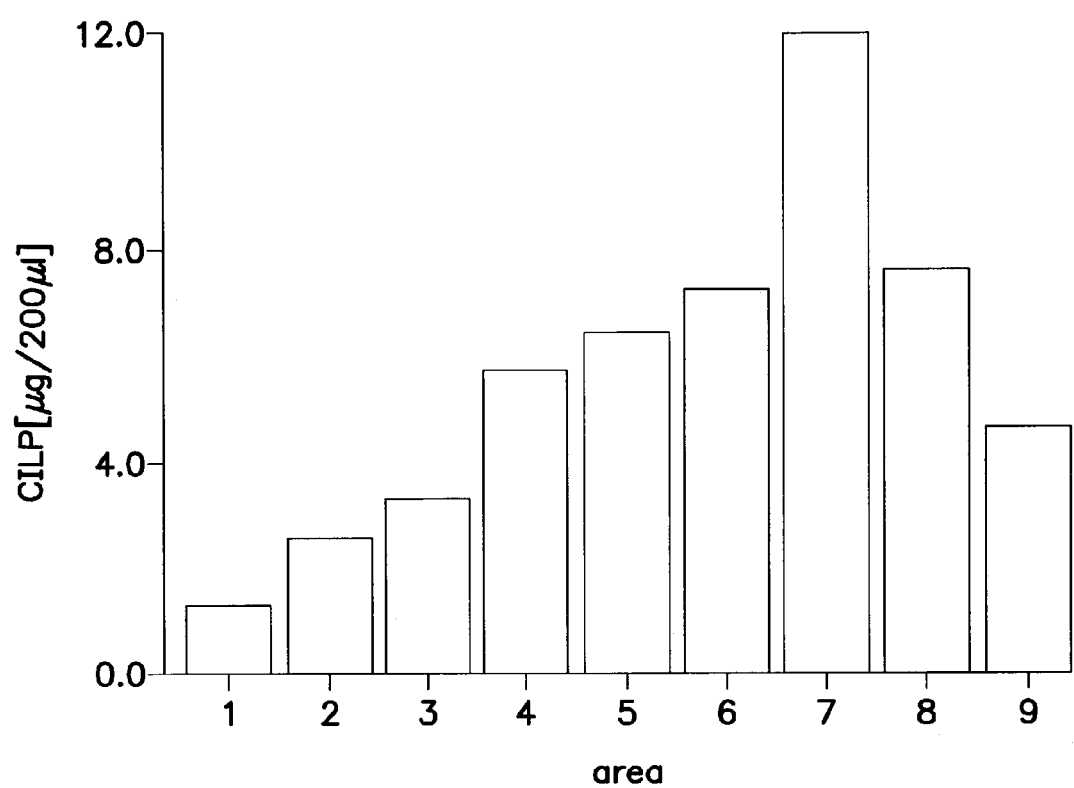

FIG. 5 shows the CILP content in different layers of human articular cartilage.

Figure 6:
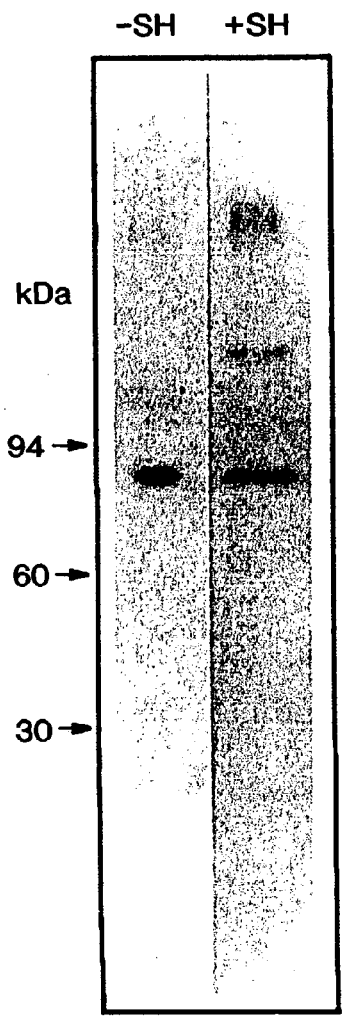

FIG. 6 shows synthesis of CILP by articular chondrocytes in explant cultures. –SH indicates non-reducing SDS-PAGE; +SH indicates reducing SDS-PAGE.

Figure 7:
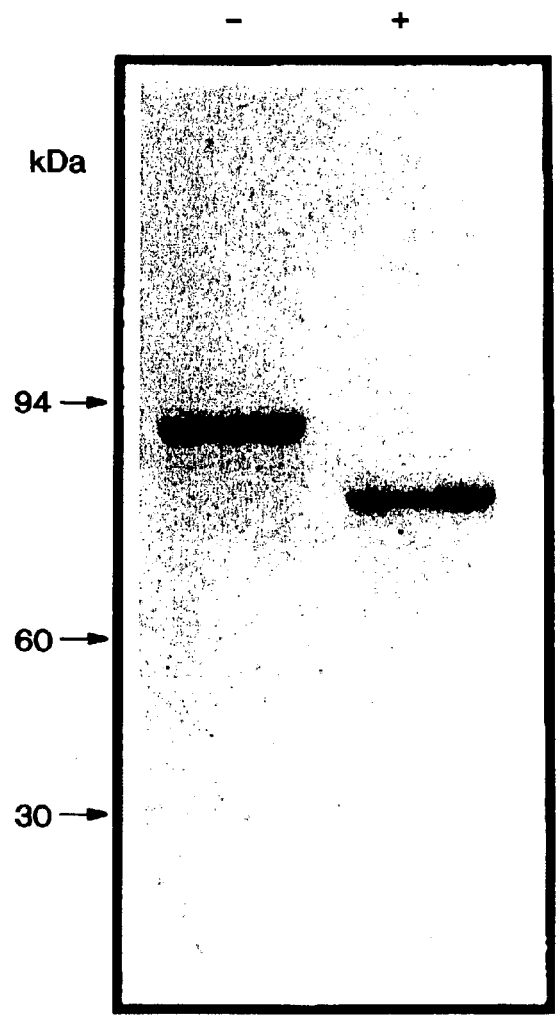

FIG. 7 shows the results of deglycosylation of CILP by N-glycosidase F digestion (8% SDS-PAGE/Coomassie).

Figure 8A:
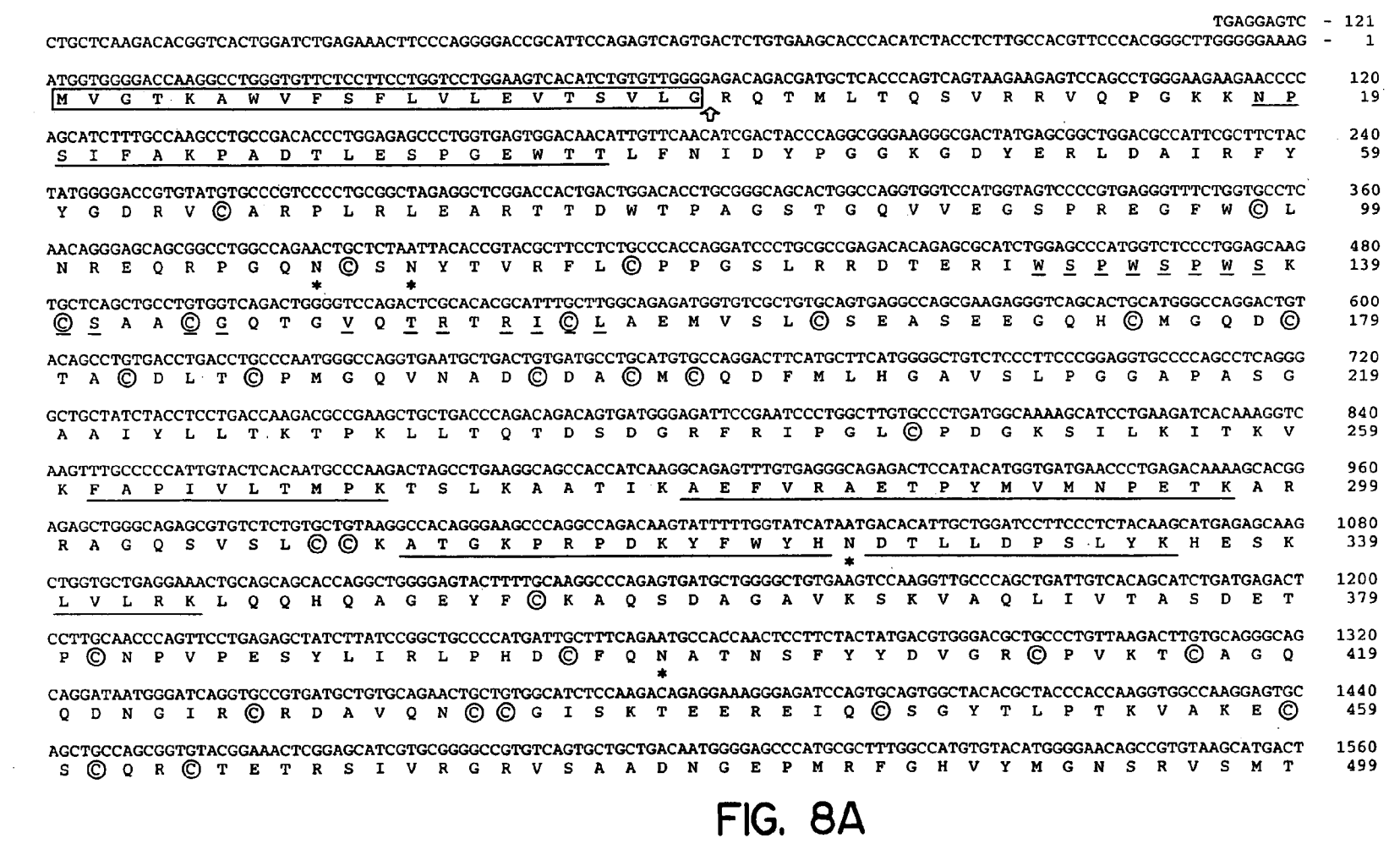
Figure 8B:
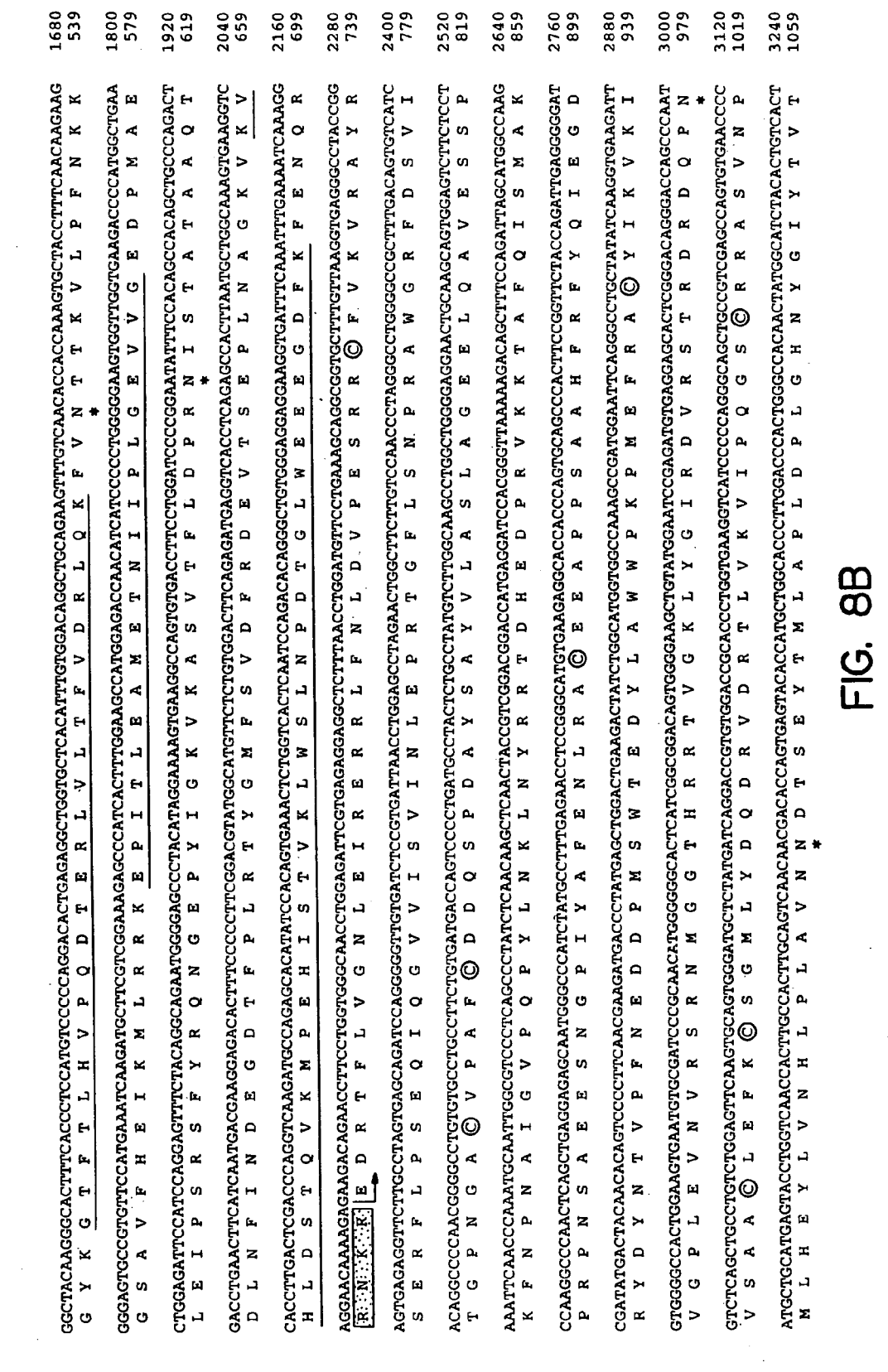

FIG. 8 shows CILP nucleotide (SEQ ID NO:1) and translated amino acid (SEQ ID NO:2) sequences. Panel 8B is a continuation of panel 8A, and panel 8C is a continuation of panel 8B. The putative signal peptide is boxed. The arrows indicate the putative cleavage site. The underlined amino acids represent peptides that were sequenced (see Table 1). The cysteines are circled, and the putative N-glycosylation sites are marked with a star. The stop codon is marked and the polyadenylation signals are underlined. The sequence homologous to porcine NTPPHase is shown in FIG. 8B beginning at residue 704 and is marked by an arrow. The Type I thrombospondin repeat sequence consensus is identified at residues 131–157, with conserved residues underlined.

Figure 9:
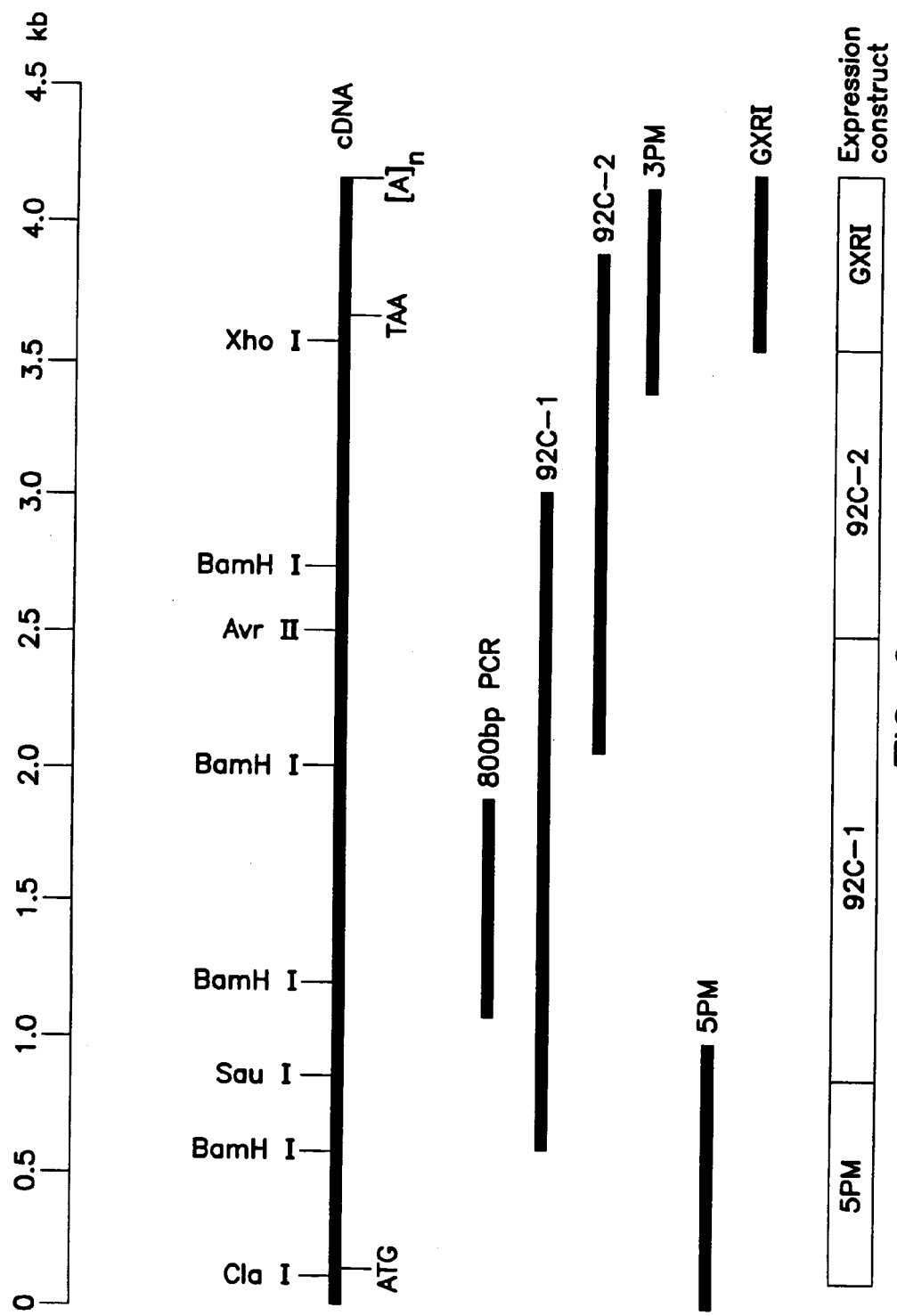

FIG. 9 is a schematic representation of the organization of the CILP cDNA. The scale in kb is shown at the top. The second line displays the cDNA size. The locations of the restriction sites are indicated. ATG is the first initiation codon for translation, TAA is the termination codon for translation, $[A]_n$ indicates the location of the poly(A) tail. The overlapping cDNA clones and the genomic clone are shown with respect to the schematic structure of the cDNA. The expression construct is shown at the bottom, with the different clones used.

Figure 10:
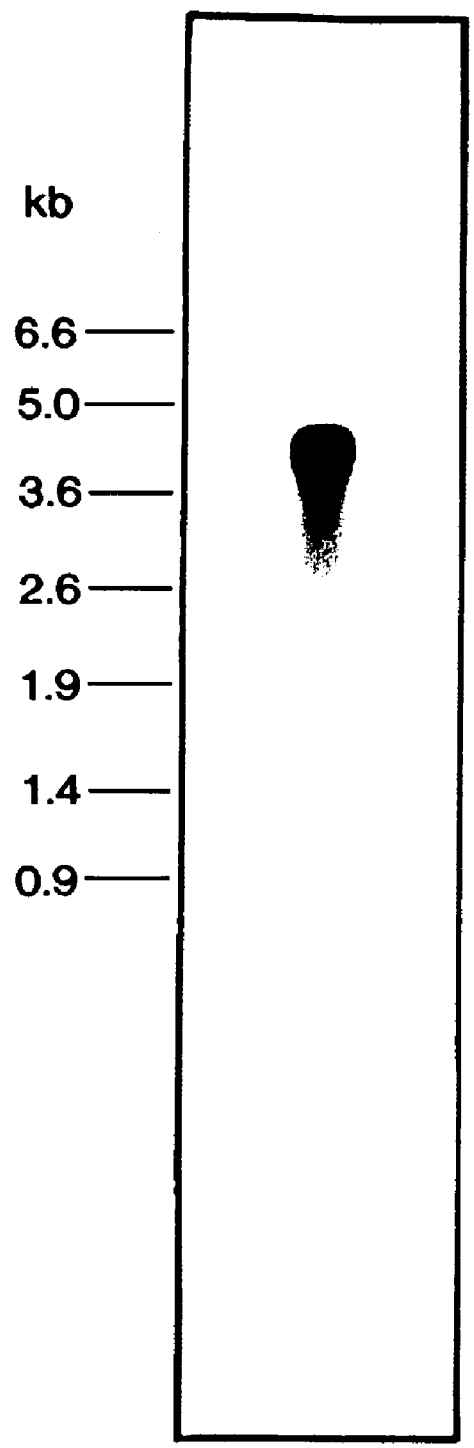

FIG. 10 shows the results of Northern blot analysis of CILP mRNA. Total RNA (10 μg) extracted from human articular chondrocytes were analyzed by Northern blotting using the $[\beta^{32}P]dCTP$ probe of a 1585-bp BsmI/EcoRI fragment from the 92C-1 clone. RNA size standards are indicated on the left.

FIG. 11 shows the expression of the full-length cDNA in vitro and in COS-7 (in vivo).

A. pBluescript II KS(+) with the expression construct was in vitro transcribed-translated by the TNT® T3 Coupled Reticulocyte Lysate Systems in the presence of $[^{35}S]$methionine. The in vitro synthesized polypeptide was resolved on a 4–16% gradient SDS-Polyacrylamide gel and visualized by fluorography. Lane 1: Control plasmid only. Lane 2: Plasmid with the expression construct.

B. COS-7 cells were transfected with the pSVL vector containing the expression construct and grown in a serum-free medium containing $[^{35}S]$methionine. After labeling, the cell extract was immunoprecipitated with the antibodies against CILP. The immunoprecipitated material was resolved on a 4–16% gradient SDS-Polyacrylamide gel and visualized by fluorography. Lane 1: Transfection with the vector only. Lane 2: Transfection with the vector containing the expression construct. The molecular weight standards are indicated on the left.

C. COS-7 cells were transfected with the pSVL vector containing the expression construct and grown in a serum-free medium containing $[^{35}S]$methionine. After labeling, the medium was immunoprecipitated with the antibodies against CILP. The immunoprecipitated material was resolved on a 4–16% gradient SDS-Polyacrylamide gel and visualized by fluorography. Lane 1: Transfection with the vector only. Lane 2: Transfection with the vector containing the expression construct. The molecular weight standards are indicated on the left.

FIG. 12 shows the expression of the full-length cDNA in EBNA cells. EBNA cells were transfected with the pCEP 4 vector containing the expression construct. Proteins in the medium were precipitated with ethanol and resolved on a 4–16% gradient SDS-Polyacrylamide gel and transferred to nitrocellulose membranes by diffusion.

A. Membranes were probed with polyclonal antibodies against CILP.

B. Membranes were probed with polyclonal antibodies against the homolog to the N-terminal of NTPPHase.

In both panels, the proteins were visualized by a chemiluminescent system. Lane 1: CILP isolated from articular cartilage. Lane 2: transfection with the vector only. Lane 3: transfection with the vector containing the expression construct.

The molecular weight standards are indicated on the left.

DETAILED DESCRIPTION OF PREFERRED EMBODIMENTS

Reference will now be made in detail to the present preferred embodiments of the invention, examples of which are illustrated in the accompanying drawings.

The present invention provides a novel articular cartilage matrix protein, CILP, analogs and homologs of CILP, and portions (fragments) of CILP and its analogs and homologs. The amino acid sequence of human CILP is presented in FIG. 8 and SEQ ID NO: 2. Fragments of CILP can be identified and produced using this sequence as a guide. As used herein, "peptide" or "polypeptide" or "protein" refers to a polymer in which the monomers are alpha amino acids joined together through amide bonds. Peptides are two or more amino acid monomers long. Polypeptides are more than ten amino acid residues in length. Proteins are more than thirty amino acid residues in length. Thus, peptides include polypeptides and proteins, and polypeptides include proteins. Standard abbreviations for amino acids are used herein.

Analogs include all proteins, polypeptides, or peptides that show substantial chemical and functional similarity to CILP, and can include CILP with post-translational modifications not necessarily present in the CILP as purified (e.g., glycosylation at sites not glycosylated in the protein as purified, or proteins containing no glycosylation at sites ordinarily glycosylated), or as found in nature. In embodiments, the analogs comprise CILP that has been chemically modified. In preferred embodiments, the CILP has been modified to improve a desirable characteristic, for example, immunogenicity, cell adhesion, cell permeability, or stability. For example, cyclic peptides can be made to optimize the interaction site. In other embodiments, the analog is modified such that it can be detected more readily, for example, by including a label in the modified structure. Chemical modification can include any type of modification to the base molecule envisioned by the skilled artisan, as long as the resulting molecules retains essentially all of its assayable characteristics. In other words, the molecule must still be recognizable, by standard biochemical assays used in the art, as a CILP. Analogs can have multiple additional functions beyond those of natural CILP, including non-natural enzymatic and/or cell binding activity, or can have fewer functions.

Homologs include CILP from all mammals, including, but not limited to, humans, bovine, murine, monkeys, apes, ungulates, felines, and canines. Homologs also include those of insects and lower eukaryotes (e.g., yeast) as well. Homologs also include all proteins showing high levels of identity, but slightly different tissue distribution and/or biochemical activity. A high level of identity is at least 50% identity, calculated over the entire length of the protein, polypeptide, or peptide of the invention. For example, a homolog can have at least 60% identity with the protein, polypeptide, or peptide of the invention, at least 65% identity, at least 70% identity, at least 75% identity, at least 80% identity, at least 85% identity, at least 90% identity, at least 95% identity, at least 98% identity, or at least 99% identity. A homolog can have 100% identity with the protein, polypeptide, or peptide of the invention. Percent identity can be calculated using the BLAST sequence analysis program suite, Version 2, available at the NCBI (NIH). It is well-known in the art that essentially all proteins found in a mammal has at least one homolog in another mammal, and an overwhelming majority of mammalian proteins have homologs in other animals and insects. The state of the art in the field of molecular biology now is that, given a specific protein (or nucleic acid) sequence, it is a routine matter for one of skill in the art to identify and isolate homologs of that protein (or nucleic acid).

Fragments are portions of a peptide, polypeptide, or protein. Fragments contain less than the entire amino acid sequence of the peptide, polypeptide, or protein from which they are derived. Fragments can be generated by any known technique, including expression of a nucleic acid construct encoding the fragment, chemical/enzymatic cleavage of the CILP, or total chemical synthesis of a selected fragment, based on the sequence of FIG. 8 and SEQ ID NO:2. Fragments can be any of those encompassed by the sequence of FIG. 8 and SEQ ID NO:2, but are preferably fragments that show immunoreactivity with antibodies (polyclonal and monoclonal) that specifically react with a CILP. Fragments can also be identified by their ability to react with antibodies that specifically react with CILP analogs and homologs.

The proteins, polypeptides, or peptides of the invention, can be isolated and/or purified from any eukaryote in which they are naturally present, including, but not limited to, mammals such as humans, dogs, cats, monkeys, apes, horses, pigs, and rodents (e.g., mice and rats). For example, because CILP) was found to be restricted in its tissue distribution to cartilage and furthermore, to specific zones within the tissue (the precursor protein is synthesized by chondrocytes and processed close to secretion), it can be purified from chondrocyte-containing tissues. Purification techniques can include any of those known to the skilled artisan, in any combination or order, that results in purification of the desired polypeptide or peptide. A preferred technique is disclosed in the Examples; however, modifications of the method are contemplated by the invention as well.

Techniques for production of proteins, polypeptides, and peptides in high amounts by genetic engineering techniques through the use of expression vectors, such as plasmids, phages, and phagemids, are well known. The proteins and fragments of the present invention can be produced by insertion of the appropriate polynucleotide into an appropriate expression vector at the appropriate position within the vector. Such manipulation of polynucleotides is well known and widely practiced by the ordinary artisan. The proteins and fragments can be produced from these recombinant vectors either in vitro or in vivo, for example, in prokaryotic cells or lower eukaryotes (e.g., yeast). In a preferred embodiment, the method for the production of a polypeptide of the invention comprises the steps of:

(a) optionally amplifying the polynucleotide coding for the desired protein or fragment using a pair of primers according to the invention by a target nucleic acid amplification method;

(b) inserting the nucleic acid of interest in an appropriate vector to create a recombinant vector;

(c) transforming or transfecting a host cell with the recombinant vector to create a recombinant (transformed) cell;

(d) culturing the recombinant cell in an appropriate culture medium;

(e) optionally separating the culture medium from the recombinant cell mass, (f) optionally lysing the recombinant cells;

(g) optionally separating or purifying, from the culture medium, or from the pellet of the resultant recombinant cell lysate, the thus produced protein or fragment of interest;

(h) optionally, characterizing the produced protein or fragment of interest.

Accordingly, the invention provides recombinant CILP) proteins, polypeptides, and peptides.

In embodiments, the method of producing the protein or fragment can be used to facilitate a method of purifying the protein or fragment, or can be a method of purifying the protein or fragment as well. The method can further include quantifying the purified protein. In addition, many techniques for purifying recombinantly-produced proteins and fragments are well-known to the skilled artisan and, thus need not be detailed here. In general, these techniques result in separation of the CILP from at least one other macromolecule originally found in a sample containing the CILP, analog, homolog, or fragment. In preferred embodiments, the techniques result in separation of the CILP, analog, homolog, or fragment from all, or essentially all, other macromolecules and/or organic molecules originally found in the sample containing the CILP. Macromolecules include, but are not limited to, polymers (e.g., proteins, nucleic acids, polysaccharides), aggregates, membranes or membrane components (e.g., lipid structures), and organelles. A CILP, analog, homolog, or fragment is essentially purified when no other macromolecules are present in the sample containing the CILP, analog, homolog, or fragment. A CILP, analog, homolog, or fragment is purified when it is the only component detectable in a sample, using standard detection methods. In preferred embodiments, the CILP, analog, homolog, or fragment is purified.

Techniques for isolation and purification include filtration, centrifugation, chromatography, and precipitation, and, in embodiments, are used to purify the protein or fragment of the invention. In embodiments, tags, such as affinity tags, are included in the protein to facilitate purification. Preferably, the tags are cleavable. Preferred techniques are described herein.

Chemical and enzymatic cleavage of proteins, and subsequent purification of the cleavage products, are well-known techniques that can routinely be applied to the proteins and polypeptides of the invention. Included in these techniques are those that cleave the polypeptides at an internal site (e.g., an endopeptidase) and those that digest the polypeptide from one or the other end (e.g. an exopeptidase). Having the sequence of FIG. 8 (and SEQ ID NO: 1 and SEQ ID NO:2), the skilled artisan can use these techniques, or combinations of these techniques, to create fragments having the exact sequence desired. Furthermore, techniques are available for chemically modifying the isolated fragments to create, for example, highly immunogenic molecules or molecules with enhanced activities.

In embodiments, fragments are short stretches of contiguous amino acids according to FIG. 8 (SEQ ID NO:2). These peptide fragments can be as short as 4 residues, for example when used as antigenic sites. Preferably, the fragments are at least 4 residues in length, for example, between 5 and 50 residues in length. More preferably, the fragments are between 5 and 40, or even between 5 and 20 residues in length. In embodiments, the fragments are longer, for example, at least 8 residues in length, at least 20 residues in length, and at least 30 residues in length. For example, fragments can be 5, 7, 9, 10, 13, 16, 17, 18, 19, 20, 21, 24, 25, or 37 amino acids in length. According to certain embodiments of the invention, a fragment can be generated from non-contiguous amino acid sequences from FIG. 8 (SEQ ID NO:2). In these embodiments, the fragment comprises at least two amino acid sequences present in FIG. 8 (SEQ ID NO:2), where each sequence contains at least 4 contiguous amino acids of FIG. 8 (SEQ ID NO:2). In preferred embodiments, such fragments contain at least one antigenic site from the full-length amino acid sequence.

Having provided naturally produced or recombinant purified and/or isolated proteins and fragments (e.g., peptides and polypeptides), the present invention accordingly provides pharmaceutical compositions comprising these molecules. Thus, in embodiments, the present invention provides a pharmaceutical composition comprising a peptide, polypeptide, or protein, or a homolog or analog according to the invention. Preferably, an acceptable physiological carrier is provided along with the polypeptide(s) and/or peptides. The acceptable physiological carrier can be any known to the skilled artisan, but is preferably selected from the group consisting of cationic biodegradable microparticles (such as glycolipidic particles), polylactide particles, polyglycolide particles, water, and a physiological saline solution.

These molecules and compositions can be used, for example, to treat individuals suffering from joint disease. The joint disease can be, but is not limited to, OA, rheumatoid arthritis, crystal deposit arthritis, psoriatic arthritis, and reactive arthritis. In embodiments, a protein or fragment of the invention is administered to an individual in a quantity sufficient to effect (achieve) the intended response. The composition may be administered to an individual one or several times with an acceptable physiological carrier and/or an adjuvant, optionally in combination with a pharmaceutically compatible excipient, such as saline buffer. The number of administrations can depend on the number required to achieve the intended response.

Among the other uses for the peptides, fragments, and analogs of the present invention are to generate specific antibodies against these molecules. Thus, the invention provides antibodies that specifically react with CILP, an analog, a homolog, or an immunoreactive fragment of CILP, an analog, or a homolog. The antibodies can be either monoclonal antibodies or polyclonal antibodies, and can be generated by any known technique, including those disclosed herein. In embodiments, polyclonal antibodies present in sera are used for detection of at least one immunogenic epitope present on the protein(s) or fragment(s) of the invention. Monoclonal antibodies can be used to detect a single epitope, of combinations of monoclonal antibodies can be used together to detect multiple epitopes.

The antibodies of the invention can be used not only to identify CILP and its analogs, homologs, and immunogenic fragments, but to determine the location and quantity of these molecules in tissues. In an embodiment of the invention, the antibodies can be used as part of a pharmaceutical composition, which can be administered to individuals.

These pharmaceutical compositions can specifically target CILP-containing cells for treatment.

In another aspect of the present invention, nucleic acids encoding CILP, its analogs and homologs, and fragments of these molecules, are provided. Included among these molecules are all nucleic acid molecules encoding the CILP sequence disclosed in FIG. 8 (i.e., all nucleic acids encoding SEQ ID NO:2). Also included are all nucleic acid molecules encoding fragments of the CILP sequence of FIG. 8 (i.e., all nucleic acids encoding fragments of SEQ ID NO:2). In addition, the present invention includes short oligonucleotide molecules encoding a portion, but not all, of the CILP of FIG. 8 (i.e., a portion of SEQ ID NO: 2). Accordingly, the invention provides nucleic acids that comprise SEQ ID NO: 1, or fragments of SEQ ID NO: 1. Nucleic acids that are complementary to the sequences described above are likewise included in the invention. In preferred embodiments, the polynucleotide comprises a nucleotide sequence present in SEQ ID NO: 1.

Short oligonucleotides can be used as probes and primers for detection and/or amplification of CILP, as well as CILP analogs and homologs, from tissues. Techniques for generating the nucleic acids of the invention are well-known and widely practiced by the skilled artisan. Probes and primers can be any length. The choice of oligonucleotide length is at the discretion of the skilled artisan, and will depend on the result desired. Examples of oligonucleotide lengths are presented in the following non-limiting examples.

In embodiments where short oligonucleotides are used, the oligonucleotides can function as either probes or primers, or both. Although for many applications, probe and primer lengths are optimally between 10 and 30 nucleotides in length, for other applications, probes and primers of greater length can be desired. Thus, according to the invention, a probe or primer should be at least 10 nucleotides in length, and is preferably at least 15 nucleotides in length. For certain applications, an oligonucleotide of between 15 and 30 nucleotides is preferred, such as one that is approximately 20–25 nucleotides in length (i.e., 20, 21, 22, 23, 24, or 25 nucleotides in length). Other applications might require an oligonucleotide that is, optimally, at least 30 nucleotides in length, such as an oligonucleotide that is approximately 50 nucleotides in length, approximately 100 nucleotides in length, or even more (e.g., 150, 200, 250, 300).

The oligonucleotides can be used to identify the presence and concentration of CILP-encoding genes or mRNA, or both, both in vivo (e.g., in situ hybridizations) and in vitro (e.g., Southern and Northern blot analyses). They can also be used to identify analogs and homologs of the sequences presented in FIG. 8 (SEQ ID NO: 1 and SEQ ID NO: 2) using known detection and screening methods, as well as study the regulation of expression of CILP and its related proteins during progression and/or treatment of joint disease.

In preferred embodiments of this aspect of the invention, recombinant vectors are provided, which contain the polynucleotides of the invention. The recombinant vectors can be any one known in the art, including, but not limited to, shuttle vectors, expression vectors, suicide vectors, and integration vectors. Exemplary vectors include plasmids, phages, phagemids, cosmids, and yeast artificial chromosomes (YACs). The recombinant vectors can be used to express the polypeptides and peptides of the invention both in vitro and in vivo, as well as to transfer the nucleic acids of the invention into host genomes. In one particular embodiment of the invention, the vectors are used in therapeutic methods, such as a method of gene therapy. In other embodiments, the vectors are used to create transgenic animals, which can be useful for the study of joint disease and the role CILP and its analogs and homologs play in the disease. For example, the transgenic animal can be used to develop and test potential drugs that ameliorate or otherwise treat OA, rheumatoid arthritis, crystal deposit arthritis, psoriatic arthritis, or reactive arthritis.

In other embodiments of the invention, compositions comprising polynucleotides and/or recombinant vectors of the present invention are provided. Gene targeting techniques can be used to introduce therapeutic polynucleotides and vectors into host cells. One of the preferred targeting techniques according to the present invention consists of a process for specific replacement, in particular by targeting the CILP gene in vivo. Such a DNA targeting technique is well known in the art and often is referred to as a "knock out" technique. According to the present invention, "knock in" techniques are contemplated as well.

Accordingly, the invention provides recombinant cells comprising the polynucleotides, vectors of the invention. The invention also provides recombinant cells comprising the proteins or fragments of the invention. The recombinant cells are host cells into which the proteins, fragments, polynucleotides (including oligonucleotides), and vectors of the invention have been introduced. Recombinant cells include progeny (i.e., offspring, daughter cells, cells directly descendent from the original transformant). The recombinant cells can be used for many purposes, including, but not limited to, expression of the proteins and fragments of the invention for purification and subsequent use in raising antibodies or treating individuals, producing a transgenic animal for the study of joint disease or for production of therapeutic compounds, and amplification of the nucleic acids, vectors, proteins, and protein fragments for use in therapeutic compositions.

Another aspect of the present invention is a kit. The kit can contain at least one protein or fragment of the invention, at least one polynucleotide or recombinant vector of the invention, and/or at least one antibody of the present invention. The kit can include one of the molecules of the invention, or multiple molecules, in any ratio or formulation. Preferably, the molecules of the invention, as well as any compositions, are contained within the kit in suitable containers such that they are stable and retain their biological activity. Preferably, the molecules and compositions contained in the kit are sterile if they are to be used for in vivo applications. In preferred embodiments, the kit of the invention contains all of the reagents and molecules necessary to utilize the kit for its intended purpose. For example, when the kit contains purified protein according to the invention for use in treatment of OA, the kit will contain not only the purified protein, but equipment necessary for administration of the protein, such as a biologically tolerable solvent in which the protein is dissolved, and a syringe for delivery of the composition.

In a preferred embodiment, the kit comprises a cartilage intermediate layer protein in a physiologically acceptable carrier, and some or all of the equipment and reagents necessary to administer the cartilage intermediate layer protein to an individual.

In general, the functional demands on different parts of articular cartilage are not fully understood. It is however known that different parts of the tissue have a different composition and structure. Thus, in the superficial region of the tissue, the collagen fibers are thinner and the relative abundance of aggrecan is much lower. In contrast, contents of decorin and COMP are higher than in the remainder of the tissue. Cells in the deeper layer elaborate thicker collagen fibers that are arranged in a different direction to those in the surface layers and the deep zone also has a higher aggrecan content. However, there have been no previous descriptions of a protein, like CILP, that can be used to define an intermediate layer of the tissue. It is an enigma why a specific protein is required to satisfy the functional demands of the tissue in this layer, and the characteristics of the protein offer no explanation.

As shown in the figures, and discussed in detail below, it is clear that CILP is synthesized and deposited in the extracellular matrix by the chondrocytes. Its absence from other tissues is also of interest and is further evidence suggesting that the protein has a specific function in cartilage breakdown or repair. The restricted distribution of the protein to the interterritorial compartment (as disclosed herein) also indicates that it has a possible role in maintaining (or destroying) the structure of the tissue rather than in the regulation of cellular activities.

It is of interest to note that CILP is one of four proteins whose expression is particularly enhanced in the early stages of human osteoarthritis. This might indicate a specific role for the protein in tissue repair or destruction. In addition, this observation serves as the basis for a further aspect of the invention. In this aspect of the invention, methods of early detection of bone and/or cartilage associated diseases are provided. For example, in a preferred embodiment of this aspect of the invention, the molecules and compositions of the invention are used in a method of early detection of osteoarthritis. Because CILP is upregulated in the early stages of OA, detection of abnormal levels of the molecules according to the invention can be used as a marker for OA. In preferred embodiments, the molecules and compositions are used to detect OA prior to any outward clinical symptoms of the disease are detectable.

In embodiments, the method of early detection of joint disease is used to detect abnormal levels of CILP in cartilage tissue. In preferred embodiments, the method is used to detect abnormal CILP levels in a cartilage matrix or in multiple cartilage matrices. The method can be used to detect abnormally low or abnormally high levels of CILP expression, but it is preferred that the method detects abnormally high levels of CILP expression. In preferred embodiments, the method can be used for early detection of cartilage disease by determining the levels of released CILP protein fragments from joint cells. A level that is abnormal compared to the average level determined for individuals known not to be suffering from joint disease is an indicator that the tested individual is suffering from a joint disease, even if no outward clinical symptoms of the disease are evident in the individual. For example, the method can be detect an increase in release of CILP or fragments of CILP into the synovial fluid, indicating that the sample was isolated from an individual in the early stages of osteoarthritis.

In addition, the method of early detection can be performed with any of the molecules of the invention described above, and can detect a multitude of joint diseases, including those described herein. For example, the method can utilize the CILP protein or its fragments, antibodies that specifically react with CILP, or nucleic acids encoding CILP or a portion of CILP. Use of the nucleic acids of the invention in the method of early detection can include detection of CILP-specific mRNA.

In a preferred embodiment, the method of early detection of OA includes:

a) isolating cartilage tissue from an individual suspected of having OA;

b) detecting the amount of CILP-specific molecules in the sample; and c) comparing the amount detected to an amount detected in a similar sample obtained from cartilage tissue from an individual known not to have OA.

The step of detecting can include using labelled antibodies that are specific for CILP or an immunogenic fragment thereof. It can also be performed using short labelled oligonucleotide probes to detect CILP-specific mRNA levels. Detection can also be performed with oligonucleotides used as primers to amplify CILP-specific mRNA to quantitate the amount present in the sample. Oligonucleotide primers can also be used to amplify and sequence the CILP mRNA to determine whether the CILP message encodes a mutant form of the protein.

EXAMPLES

The invention will be further clarified by the following Examples, which are intended to be purely exemplary of the invention, and should not be construed as limiting the invention in any way.

Example 1

Extraction of Cartilage

Human articular cartilage was obtained at surgery after total hip replacement for femoral neck fracture. The cartilage was dissected clean, sliced into fine pieces and disrupted using a high speed homogenizer (Polytron, Kinematica GmbH, Kriens-Lusern, Switzerland) in 12 volumes (w/v) of 0.15 M NaCl, 0.05 M sodium phosphate, pH 7.4, also containing a protease inhibitor cocktail (5 mM benzamidine hydrochloride, 0.1 M 6-aminohexanoic acid), and 5 mM N-ethylmaleimide, as described by Heinegård and Sommarin, ("Isolation and characterization of proteoglycans", 1987, *Methods Enzymol.* 144:319–372). The mixture was pre-extracted 4 hours at 4° C. then centrifuged at 20,000×g and 4° C. for 30 minutes. The pellet was extracted with 12 volumes (w/v) of 4 M guanidine hydrochloride (GdnHCl), 0.05 M sodium acetate, pH 5.8, containing the protease inhibitor cocktail, 5 mM N-ethylmaleimide and 10 mM EDTA, for 24 hours at 4° C. followed by centrifugation at 20,000×g at 4° C. for 30 minutes.

Proteins in the extract were separated from proteoglycans by CsCl-density gradient centrifugation with a starting density of 1.5 g/ml under dissociative conditions 4 M GdnHCl (Heinegård and Sommarin, 1987, supra). The gradient tube was divided into 4 equal fractions using a Beckman tube slicer, and the top two fractions (D3 and D4) were used for subsequent purification.

Example 2

Protein Purification

The pooled fractions from the CsCl-gradient (D3 and D4) were concentrated by ultrafiltration (PM-10 membrane, Amicon, Inc. Beverly, Mass., USA), followed by diaflow against 7 M Urea, 20 mM Tris-HCl, pH 8, and then chromatographed on a column of DEAE-cellulose (5×10 cm, DE52, Whatman, Maidstone Chemicals, Kent, United Kingdom) equilibrated with the urea buffer. After sample loading, the column was washed with 5 bed volumes of the equilibration buffer, and eluted with a linear gradient (2×800 ml) from 0 to 1 M NaCl. Selected fractions were analyzed by SDS-PAGE for the presence of CILP. One pool of the protein was bound to the DEAE column and eluted at 0.04 M of NaCl, while the rest of the protein was in the flow-through. This flow-through material was mixed with an equal volume of 20 mM sodium acetate, and the pH was adjusted to 5. Then the protein was further purified on a CM 52 column (1.6 cm×15 cm, Carboxymethyl-cellulose, Whatman Maidstone Chemicals, Kent, United Kingdom), equilibrated in 7 M Urea, 10 mM sodium acetate pH 5 at 20 ml/hr. After loading the sample, the column was washed with 5 bed volumes of equilibration buffer followed by elution with a linear gradient of 0 to 0.5 M NaCl. Fractions of 10 ml were collected, monitored for protein content by measuring their absorbance at 280 nm, and analyzed by SDS-PAGE.

The fractions containing CILP were pooled and concentrated by ultrafiltration, followed by diaflow against 4 M GdnHCl, 50 mM sodium acetate, pH 5.8 and further chromatographed on two serially coupled FPLC gel filtration columns of Superose 6 and Superdex 200 (Pharmacia Biotech, Uppsala, Sweden) equilibrated and eluted at 0.2 ml/min with 4 M GdnHCl, 50 mM sodium acetate, pH 5.8. Fractions of 0.5 ml were collected and monitored for protein content by measuring their absorbance at 280 nm. Protein patterns were analyzed by SDS-PAGE.

Early attempts to purify CILP from human articular cartilage involved direct extraction of the cartilage with the GdnHCl solution. However, the abundant albumin in the preparation masked a pool of CILP that was bound to the DEAE column. This pool eluted at a very low salt concentration (0.04 M NaCl), while the remainder of CILP appeared in the flow through, as discussed above. Preliminary studies were done using protein in the 0.04 M NaCl pool purified by CM52 chromatography and gel filtration. In a subsequent study investigating the component which bound to DEAE, the tissue was pre-extracted with phosphate buffered saline at pH 7.4, containing a protease inhibitor mix, to remove the albumin and other proteins not tightly held in the cartilage matrix.

The two pools of CILP, i.e. the one bound to the DEAE and the one in the flow through, showed identical peptide patterns after trypsin digestion when analyzed by reverse phase HPLC (C-18) (data not shown). The two protein variants also appeared to have a similar content of N-linked oligosaccharides since their respective mobilities upon SDS-PAGE before and after N-glycanase digestion were identical (data not shown). No further experiments were done to elucidate the difference between the two proteins. All the biochemical studies were done using the protein pool from the CM-cellulose chromatography, even though the two pools appeared to contain the same protein.

Example 3

Sodium Dodecyl Sulfate-Polyacrylamide Gel Electrophoresis (SDS-PAGE)

Electrophoresis was performed as described by Laemmli (Laemmli, U. K., 1970, *Nature* 227:680–685) on gradient polyacrylamide (4–16%) slab gels with a 4% polyacrylamide stacking gel. Samples of the fractions were precipitated with 10 volumes of ethanol containing 50 mM sodium acetate and recovered after centrifugation as described elsewhere (Paulsson, M., Sommarin, Y. and Heinegård, D., 1983, *Biochem. J.* 212:659–667). Precipitates were dissolved in electrophoresis sample buffer (2% SDS, 0.125 M Tris-HCl, pH 6.8, 0.002% Bromophenol blue and 20% Glycerol) either with or without 10% 2-mercaptoethanol, incubated at 37° C. for 30 minutes, boiled at 100° C. for 4 minutes, and electrophoresed. Gels were stained with Coomassie Brilliant Blue R (Serva, Heidelberg, Germany). CILP was pure as judged by this sodium dodecyl sulfate-polyacrylamide gel electrophoresis. By this procedure a yield of 129 μg of CILP per gram of tissue wet weight was obtained. The relative mobility of CILP on SDS-PAGE was not significantly affected by reduction, which suggested a monomeric protein (data not shown).

The molecular mass of the purified CILP protein was estimated by running linear SDS-PAGE with concentrations ranging from 6% to 12% polyacrylamide (i.e., 6, 8, 10, and 12% SDS-PAGE) (Heinegård, D. and Sommarin, Y., 1987, supra). A Ferguson plot was constructed (Ferguson, K. A., 1964, *Metabol. Clin. Exp.* 13:985–1002) from the relative mobilities of CILP and reference proteins. Molecular mass was determined from the retardation coefficients ($K_1$) as described by Banker and Cotman (Banker, G. A. and Cotman, C. W., 1972, *J. Biol. Chem.* 247:5856–5861). The Cotman plot suggested an ideal behavior and the molecular mass determined was 91,500 (data not shown).

Example 4

Preparation of Antibodies

1. Antibodies were raised in rabbits by using CILP purified from the gel filtration separation. The protein (100 μg) was solubilized in 0.15 M NaCl, 5 mM sodium phosphate, pH 7.4, mixed with an equal volume of Freund's complete adjuvant (Difco Laboratories, Detroit, Mich., USA), and injected at multiple sites subcutaneously in the back. Booster doses (100 μg) in Freund's incomplete adjuvant (Difco Laboratories, Detroit, Mich., USA) were given twice, at one month intervals.

2. A synthetic peptide (EDRTFLVGNLEIRERRLF; SEQ ID NO:3) spanning amino acid residues 684–701 corresponding to the human homologous N-terminal of NTP-PHase (FIG. 9) was coupled to KLH (Saveen Biotech AB, Malmö, Sweden), and used to generate a rabbit polyclonal antiserum using known techniques.

Example 5

Immunoassays

Immunoblot

Articular cartilage from different mammalian species (bovine, equine, canine, murine—Swarm rat chondrosarcoma, and human) was extracted with 15 volumes of 4 M GdnHCl containing protease inhibitors, as described above. Aliquots of the extracts corresponding to 2 mg of tissue wet weight, were precipitated twice with 10 volumes of ethanol as described by et al., 1983, supra. Extracts were electrophoresed on two identical 4–16% gradient SDS-PAGE under non-reducing conditions, with a sample of purified CILP electrophoresed for comparison. One gel was stained for protein with Coomassie Brilliant Blue-R. Proteins were transferred from the other gel to a nitrocellulose membrane (Hybond-C, Amersham, England) by diffusion (Bowen, B., Steinberrg, J., Laemmli, U. K., and Weintraub, H., 1980, *Nucleic Acids Res.* 8: 1–20) for immunodetection. The membrane was blocked for 1 hour with 5% nonfat dry milk in 10 mM Tris-HCl pH 7.4, 0.15 M NaCl, 0.2% Tween 20, and incubated with antibodies to CILP diluted 1:500 in 10 mM Tris-HCl pH 7.4, 0.15 M NaCl, 0.2% Tween 20 and 0.1% BSA. Bound antibodies were detected with anti-rabbit IgG peroxidase conjugate (Dakopatts, Copenhagen, Denmark) diluted 1:500 in the same buffer as the primary antibody. Enzyme activity was detected using $H_2O_2$/diaminobenzidine containing cobalt chloride and ammonium nickel sulfate (De Blas, A. and Cherwinski, M., 1983, *Anal Biochem.* 133:214–219).

Specificity of Antibodies Against CILP.

Figures 1A, 1B:
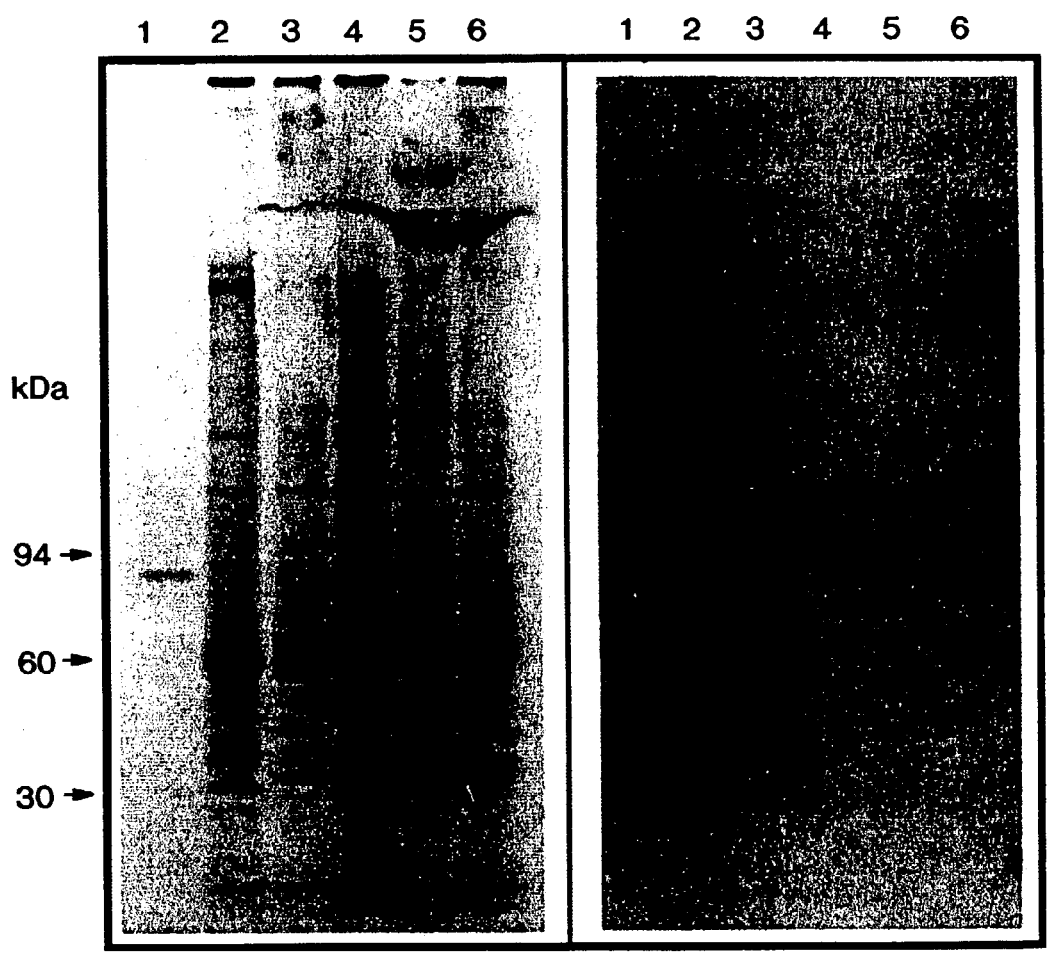
FIG. 1 shows the results of an immunoblot analysis of CILP in extracts of articular cartilage of different species.

To determine the specificity of the antibodies, an aliquot of the guanidine-hydrochloride extracts from different species (human, bovine, murine, canine, equine) were precipitated with ethanol, electrophoresed on SDS-PAGE, and transferred onto nitrocellulose membranes. An immunoreactive band corresponding to the relative mobility of CILP was detected in the extracts (FIG. 1). No positive staining was, however, observed in the extract of the Swarm rat chondrosarcoma. There were differences in the relative intensities of the band in the various tissues, although the protein staining indicated that a similar amount of the extracts was loaded onto each lane. The observed differences might result from limited cross-reactivity or might indicate a variable abundance of the protein.

Enzyme-Linked Immunosorbent Assay (ELISA).

The assays were performed essentially as previously described (Larsson, T., Sommarin, Y., Paulsson, M., Antonsson, P., Hedbon, E., Wendel, M., and Heinegård, D., 1991, *J. Biol. Chem.* 266:20428–20433). CILP was coated onto NUNC gamma-irradiated polystyrene microtiter plates (Immunoplate I, NUNC, Roskilde, Denmark) at 0.5 μg/ml in 4 M GdnHCl, 50 mM sodium carbonate, pH 10, by incubation overnight at room temperature (approximately 22° C.). After rinsing with 0.15 M sodium chloride, 0.05% (w/v) Tween 20, the plates were coated with 2 mg/ml bovine serum albumin (Serva, Fine Biochemicals, Heidelberg, Germany) in phosphate buffered saline, pH 7.4, for 1 hour.

Samples of human tissues were extracted with 15 volumes of 4 M GdnHCl containing protease inhibitors as described above. The extracts were precipitated twice with ethanol (Paulsson, et al., 1983, supra) and resuspended in 0.8% SDS in 10 mM phosphate buffered saline pH 7.4, to give stock solutions corresponding to 4 mg of the original tissue wet weight per ml. Dilutions were made from these stock solutions and added to an equal volume of antiserum in 4% (v/v) Triton X-100, 0.01 M sodium phosphate, pH 7.4. After pre-incubation for one hour at room temperature, this mixture was added to the coated wells of the microtiter plates. After 1 hour, plates were rinsed and bound antibodies were detected using a swine anti-rabbit alkaline phosphatase conjugate (Orion Diagnostica, Helsinki, Finland) with p-nitrophenyl phosphate (Sigma Chemical Co, St. Louis, Mo., U.S.A.) as the substrate.

A standard curve using purified CILP in 0.8% (w/v) SDS, 10 mM phosphate buffered saline pH 7.4, was included in each microtiter plate. All samples were analyzed in triplicate and the mean value was used for calculations.

Distribution of CILP Among Human Tissues and with Age Variation

GdnHCl extracts were prepared from various tissues, and the presence of CILP was determined using an enzyme linked immunosorbent assay (FIG. 2). All the cartilage extracts analyzed gave inhibition curves parallel to the standard, showing that the assay actually measured the same protein with no interfering substances. The concentration of CILP was calculated to be 129 ng/mg tissue wet weight for articular cartilage, 62 ng/mg for tracheal cartilage, and 983 ng/mg for rib cartilage. It was apparent that the non-cartilaginous tissues analyzed (liver, kidney, intestine, lung, skin, aorta, muscle, tendon, bone) did not contain detectable amounts of the protein. The high concentration of the protein in rib cartilage is intriguing. Similarly, the relatively low levels in tracheal cartilage should also provide clues to the function of CILP.

Analysis of the CILP content in articular cartilages from individuals of different ages showed considerably lower values in the younger individuals (FIG. 3). After cessation of growth, the levels of the protein were quite variable, but in general they were higher than in the younger individuals. Thus, CILP levels in articular cartilage increases with age. Similarly, there is considerable evidence in the art to support the accumulation of matrix aggrecan during normal aging of articular cartilage. The increasing concentration of CILP with age might, like in the case of aggrecan, reflect a slow turnover of the protein, particularly in the interterritorial matrix.

Immunohistochemistry and Immunolocalization

Normal appearing human articular cartilage from a 38 year old hip joint was obtained from autopsy. Full-depth plugs of cartilage, 4 mm in diameter, were excised using a cork borer. The cartilage was frozen, embedded in O.C.T. compound (Tissue Teck II, Miles laboratories, Naperville, Ill., USA) and sectioned at –25° C. in a cryostat. Cryosections (5 μm) were transferred onto gelatin-coated glass slides, dried at room temperature for two hours, fixed at 4° C. with cold acetone for 10 minutes, and re-hydrated in phosphate buffered saline (PBS). To increase antibody permeability, the sections were digested for 30 minutes at room temperature with 2 mg/ml of hyaluronidase (from bovine testes, type I, Sigma, St. Louis, Mo., USA) in PBS, pH 5. Endogenous peroxidase was quenched by incubating in PBS containing 1% (v/v) $H_2O_2$ for 20 minutes at room temperature. After rinsing three times with PBS-0.1% (w/v) BSA, each section was incubated with goat-serum diluted 1:70 in PBS-0.1% (w/v) BSA for 20 minutes to reduce non-specific binding. Sections were then incubated with the primary antibody against CILP (diluted 1:800 with PBS-0.1% BSA) or with preimmune rabbit serum (diluted 1:400 with PBS-0.01% BSA) at 4° C. overnight in a moist chamber. After rinsing three times with PBS-0.01% BSA, the sections were treated with biotinylated second antibody (diluted 1:200) and avidin peroxidase conjugate using the vectastain ABC kit (Vector Laboratories, Burlingame, Calif., USA), according to the protocol of the manufacturer.

The protein was detected primarily in the middle zone, while it was less prominent or absent at the superficial and the very deepest zones of the articular cartilage (FIG. 4). The antibodies primarily stained the interterritorial matrix of the tissue, while low or no reactivity was seen in the pericellular matrix of the chondrocytes. Based on its immunolocalization this protein was named Cartilage Intermediate Layer Protein (CILP).

CILP Content in Different Layers of Articular Cartilage

To further characterize the CILP localization within the articular cartilage, sections parallel to the cartilage surface were made. Normal appearing human articular cartilage was obtained from a 38 year old femoral head at post-mortem. Full-depth plugs of cartilage, 4 mm in diameter, were excised using a cork borer and sectioned in cryostat at –25°

C. Slices 20 μm-thick were cut parallel to the cartilage surface, and each ten consecutive sections were pooled to represent 200 μm. This procedure provided 9 pools from the articular surface to the subchondral bone. The slices were extracted with 200 μl of 4 M GdnHCl, 0.05 M sodium acetate, pH 5.8, containing the protease inhibitor cocktail and 5 mM N-ethylmaleimide as described above. The extracts were precipitated twice with ethanol (Paulsson et al., 1983, supra) and the CILP content in each pool was determined by ELISA as described above.

The CILP content of the nine layers of 250 μm from the articular surface to the subchondral bone was determined by ELISA as shown in FIG. 5. Even though there were detectable amounts of CILP throughout the cartilage depths, the middle layers showed the highest content.

Immunoprecipitation

To determine whether the protein is a true cartilage constituent synthesized by the chondrocytes, human knee articular cartilage explants were metabolically labeled with [$^3$H]leucine and [$^{35}$S]sulfate. Human articular cartilage (femoral head) was obtained at surgery for hip replacement, dissected under sterile conditions and placed (25 mg tissue/ml medium) in Ham's F-12 culture medium (Gibco BRL, Grand Island, N.Y., USA), pH 7.4, supplemented with 10% (v/v) fetal calf serum and 25 μg/ml of ascorbate. The explants were metabolically labeled with 50 μCi/ml of [$^3$]leucine and 25 μCi/mil of [$^{35}$S]sulfate (Amersham International, Bucks, UK) for 4 hours at 37° C. under 5% $CO_2$: 95% air. After labelling, the explants were washed with medium without isotopes, wiped dry, and extracted with 4M GdnHCl, as described above. An aliquot of the extract was precipitated with ethanol and dissolved in 60 μl of 10 mM phosphate buffered saline, pH 7.4, containing 0.8% (w/v) SDS. To bind excess SDS the sample was then mixed with 60 μl of 2% (v/v) Triton X-100 in the same buffer. Rabbit immune serum (30 μl) was immediately added and the sample was incubated overnight at 4° C. Immunoglobulins and bound antigen were then adsorbed onto protein-A Sepharose (30 μl) (Pharmacia, Uppsala, Sweden) by incubation for 4 hours at 4° C. Bound material was recovered by centrifugation, washed, resuspended in electrophoresis buffer, and electrophoresed as above.

Radiolabelled proteins were detected by fluorography. The polyacrylamide gels were washed in distilled water for 30 minutes, soaked in 5 volumes of 1.3 M sodium salicylate for 35 minutes, dried on a gel drier (LKB Bromma, Sweden), and exposed to a preflashed Kodak XAR-5 film for 3–4 weeks at −80° C.

As shown in FIG. 6, a major band with a relative mobility corresponding to CILP was identified by fluorography after SDS-PAGE under reducing and non-reducing conditions. However, after reduction, two higher molecular weight components were also immunoprecipitated. They might represent either aggregates of CILP or possibly cross-reactivity with some related proteins or nonspecific reactivity that is sometimes observed at that position with other rabbit antisera (data not shown).

Example 6

N-Glycosidase F and O-Glycosidase Digestions

Samples to be digested were precipitated with ethanol. For the N-Glycosidase F digestion the samples were resuspended in 0.1 M Tris-HCl, pH 6.8 containing 0.1% SDS, and incubated in a boiling water bath for 3 minutes. Then an equal volume of 0.125 M Tris-HCl pH 6.8 was added, plus 5 μl of 0.5% Nonidet P40, 1 μg of trypsin inhibitor (from chicken egg white type H-0, Sigma, St. Louis, Mo., USA) and 0 Unit of enzyme (PNGase F, Boehringer Mannheim, Gmblt, Germany). Samples to be digested with O-Glycosidase were resuspended in 15 mM sodium cacodylate, pH 6.0. Trypsin inhibitor (1 μg) was added to the reaction mixture and 0.5 mU of enzyme (Boehringer Mannheim, GmbH, Germany). Deglycosylation was overnight in a water bath at 37° C.

An aliquot of the mixtures before and after digestion was diluted with sample buffer (2% SDS, 0.125 M Tris-HCl, pH 6.8, 0.002% Bromophenol blue and 20% Glycerol), boiled at 100° C. for 4 minutes and electrophoresed on a linear 8% acrylamide gel. Proteins were visualized by staining with Coomassie Brilliant Blue R (Serva, Heidelberg, Germany).

CILP contains N-linked oligosaccharides as shown by a significant change in its relative mobility after N-Glycosidase F digestion (FIG. 7). The change in mobility gives an estimate that the oligosaccharide content represents as much as 10% of the molecular mass of the protein. No apparent change in its mobility was observed after O-Glycosidase digestion (data no shown).

Example 7

Peptide Fragment Generation, Purification, and Sequencing

Proteolytic digestion with Lys-C was performed at enzyme:substrate ratios of 1:50 on a Vydac C18 column (2.1×30 mm), eluted with a gradient of acetonitrile (0–70% over 45 minutes) in 0.1% trifluoroacetic acid at a flow rate of 0.2 ml/min. Peaks were collected by hand while the effluent was monitored at 220 nm. Fourteen peptides were sequenced on an Applied Biosystems 477A automated sequencer with on-line analysis of phenylthiohydantoin-derivatives on an Applied Biosystems 120A microbore HPLC. Some peaks gave two sequences, but by analysis of the relative yields of the amino acids at each cycle, it was possible to determine both sequences with a high degree of confidence. As the protein was not reduced and carboxymethylated, no peptides were isolated that contained cysteines. Eleven of the sequenced peptides could be aligned against the translated cDNA sequence (Table 1 and FIG. 8). It should be noted that all the peptides sequenced were located within the first 680 amino acids. The N-terminal amino acid of CILP was not identified using standard techniques, suggesting that it might be blocked. Alternatively, the N-terminus might be rather heterogeneous as a result of proteolytic cleavage. One peptide (3306, Table 1) contained a blank cycle which on subsequent analysis of the translated cDNA sequence proved to be the asparagine of a carbohydrate N-linkage site. This site is, therefore, likely to contain an N-linked oligosaccharide.

TABLE 1

Amino acid sequences of CILP peptides after proteolytic digestion with Lys-C.

| Peptide | Sequence | Position at the deduced amino acid sequence |
|---|---|---|
| 3302 | AEFVDAETPYMVMNPETXK (SEQ ID NO:4) | 280–297 |
| 3304 | FAPIVLDMPK (SEQ ID NO:5) | 261–270 |

TABLE 1-continued

Amino acid sequences of CILP peptides after proteolytic digestion with Lys-C.

| Peptide | Sequence | Position at the deduced amino acid sequence |
|---|---|---|
| 3305 | NPSIFAK (SEQ ID NO:6) | 18–24 |
| 3306 | YFWYHXTTLLDPSLYK (SEQ ID NO:7) | 320–335 |
| 3307 | GTFTLHVPQDTERLVLTFVDRLQK (SEQ ID NO:8) | 483–506 |
| 3308 | PADTLESPMEXTT (SEQ ID NO:9) | 25–37 |
| 3310 | EPITLEAMETNIIPLGEVVGH (SEQ ID NO:10) | 534–553 |
| 3314 | LWSLNPDTGLEEEGXF (SEQ ID NO:11) | 657–673 |
| 3315 | LVLRK (SEQ ID NO:12) | 340–344 |
| 3317 | ATGKPRPDK (SEQ ID NO:13) | 311–319 |
| 3318 | VHLDSTQVKMPHISTVK (SEQ ID NO:14) | 639–673 |

Example 8

Cloning and Sequencing of the Gene Encoding CILP

In general, all the molecular biological procedures, including agarose gel electrophoresis, restriction enzyme digestion, ligation, bacterial transformation, and DNA sequencing, were performed by standard methods (Sambrook et al., 1989, Molecular Cloning: A laboratory manual. Cold Spring Harbor Laboratory Press, Cold Spring Harbor, N.Y.).

RNA Extraction

Human articular cartilage was obtained at surgery after total hip replacement, kept in PBS during dissection, shaved, and frozen in liquid nitrogen. Total RNA was extracted essentially as described by Adams et al. (Adams, M. E., D. Q. Huang, L. Y. Yao, and L. J. Sandell, 1992, "Extraction and isolation of mRNA from adult articular cartilage", *Anal. Biochem.* 202:89–95) but omitting the CsTFA ultracentrifugation step. Instead, the RNA was precipitated twice with 0 vol of 100% isopropanol, then further purified with a RNA easy kit (QIAGEN Inc., Chatsworth, Calif., USA) according to the manufacturer's protocol. The mRNA was purified from this preparation using the Oligotex mRNA kit (QIAGEN Inc., Chatsworth, Calif., USA) by following the manufacturer's protocol.

cDNA Probe Generation and Library Screening

Total RNA isolated from human articular cartilage was used as the template for the synthesis of the first-strand cDNA. Total RNA (20 µg) was reverse-transcribed using 400 Units of Moloney murine leukemia virus reverse transcriptase (Life Technologies) in a 50 µl reaction mixture containing 100 ng of oligo(dT), 300 ng random hexamer primers, and 1 mM dNTP, for 1 hour at 37° C. (Lee and Kaskey, 1992, "Direct complementary DNA cloning using polymerase chain reaction", *Methods Enzymol.* 216:69–72).

PCR amplification of the cDNA created in this reaction was performed with degenerate primers based on the amino acid sequences LHVPQDT (SEQ ID NO: 15), EAMETN (SEQ ID NO: 16) and PYMVMNP (SEQ ID NO:17) (forward and reverse, 1 µM each), 5 µl of cDNA, 0.2 mM dNTP mixture, 1 Unit Taq polymerase, 5 µl 10× Taq Reaction Buffer, 1.5 mM MgCl$_2$, in a 50 µl reaction mixture. After an initial denaturation step at 94° C. for 3 minutes, 35 cycles of amplification were performed in a Hybaid OmniGene thermocycler at the following conditions: 94° C. for 30 sec, 48° C. for 30 sec, 72° C. for 2 min. Ten percent of the products from the first amplification were re-amplified for an additional 25 cycles under the same cycling conditions. The PCR products were analyzed by electrophoresis on a 1% agarose gel (NuSieve GTG, FMC Corp.). The main product (approximately 800–830 bp) was subcloned into a pCR-Script Amp SK(+) (Stratagene, La Jolla, Calif., USA) and sequenced in both directions using the standard double-stranded dideoxy chain termination method. The fragment contained nucleotides 1055 to 1885 bp of the sequence disclosed in FIG. 8 (SEQ ID NO: 1). The translated sequence contained several of the determined amino acid sequences, including some of the peptide internal sequences (Table 1; FIG. 8, SEQ ID NO:2).

The fragment was used as a probe to screen a µZAPII cDNA library made from human chondrocytes (Charles et al., 1993, "Cloning, characterization, and expression of a cDNA encoding an inducible nitric oxide synthase from the human chondrocyte", *Proc. Natl. Acad. Sci. USA.* 90:11419–11423). Approximately 1×10$^6$ plaque forming recombinants were screened. One positive clone was used for further investigation (named 92C-1). The plasmid pBluescript II SK(+) containing the insert was rescued from the ZAP vector by the use of in vivo excision as described in the ZAP-cDNA® synthesis kit (Stratagene, La Jolla, Calif., USA). The plasmid was digested with XhaI/XhoI and the cDNA size (2.3 kb) was determined by electrophoresis on a 1% agarose gel (NuSieve GTG, FMC Corp.).

Restriction fragments of the cDNA were generated with BamHI and subcloned into a pCR-Script Amp SK(+). Sequencing was performed as described above, and compression artifacts were resolved using the dITP kit (USB, Cleveland, Ohio, USA). The sequencing primers used included T3 and T7 universal primers and internal sequencing primers. The 2.3 kb cDNA subclone was used to generate a 314-bp PCR probe with primers designed towards the 3' end. The probe was used for re-screening the human chondrocyte λZAPII cDNA library as described. One 1.6 kb clone (named 92C-2) was isolated, subcloned, and sequenced.

Isolation of Genomic Clones

Three genomic clones subcloned in the bacteriophage P1 were obtained from Genome Systems, Inc. screening services (St. Louis, Mo., USA). One clone containing the gene for CILP was used for isolation of a XhoI/EcoRI fragment containing the 3' end. The fragment was subcloned into pBluescript II KS(+) and used for the construction of the expression vectors.

Isolation of cDNA Ends

The Marathon cDNA amplification kit (CLONTECH) was used to obtain a library of adaptor-ligated double-stranded cDNA from human articular cartilage. One microgram of poly(A)$^4$ RNA was used as a template for the first strand synthesis as described by CLONTECH in the manual for the Marathon cDNA amplification kit, 5'- and 3'-RACE. The 5' and 3' ends were amplified using 3 µl of the library as the template with the primer supplied by CLONTECH (API) and 0.2 µM each of the gene-specific primers (RACE-5', 5'-GTACAATGGGGGCAAACTTGACCTT-3' (SEQ ID NO: 18) from 964 to 988 bp and RACE-3',5'-TCATGAA-GAGCAATGTGGGAGTAGC-3' (SEQ ID NO:19), from 3446 to 3470 bp, (FIG. 8; SEQ ID NO: 1), 0.2 mM dNTP mix, 5 µl 10× Reaction buffer and 1.25 U of Cloned Pfu DNA Polymerase (Stratagene) in a 50 µl reaction volume. After an initial denaturation step at 94° C. for 1 minute, 30 cycles of amplification were performed using the following conditions: 94° C. for 45 sec, 65° C. for 45 sec, 72° C. for 4 min. The PCR products were analyzed on a 1% agarose gel, isolated, and subcloned into pCR-Script Amp SK(+). Sequencing of both strands was performed by AmpliTaq DNA Polymerase, FS (Perkin Elmer) using fluorescent dye termination sequencing chemistry and analysis of the reaction products on an Applied Biosystems 373A DNA sequencer. The sequencing primers used included T3 and T7 universal primers and internal sequencing primers.

Example 9

Sequence Analysis

Sequence analyses were carried out using the PCGene Program package (Intelligenetics). Similarity (identity) searches were performed using the e-mail service at the National Center for Biotechnology Information and the BLAST sequence analysis program suite, Version 2, available at the NCBI (NIH). All default parameters are used. BLAST (Basic Local Alignment Search Tool) is the heuristic search algorithm employed by the programs blastp, blastn, blastx, tblastn, and tblastx, all of which are available through the BLAST analysis software suite at the NCBI. These programs ascribe significance to their findings using the statistical methods of Karlin, and Altschul, et al. (Altschul, S. F., W. Gish, W. Miller, E. W. Myers, and D. J. Lipman, 1990, "Basic local alignment search tool", *J. Mol. Biol.* 215:403–410, 1990, 1993) with a few enhancements. Using this publicly available sequence analysis program suite, the skilled artisan can easily identify polynucleotides according to the present invention.

As disclosed above, two overlapping clones (92C-1 and 92C-2, FIG. 9) were isolated by screening approximately $1 \times 10^6$ clones from a human articular chondrocyte λZAP-cDNA library. These clones encode most of the cDNA sequence for CILP (FIG. 8; SEQ ID NO:1). However, the first methionine did not conform to the Kozak consensus (Kozak, M., 1991, "An analysis of vertebrate mRNA sequences: Intimations of translational control", *J. Cell. Biol.* 115:887–903) and no signal peptide and no polyA tail was detected. No full-length clone was found after extensive re-screening of the cDNA library.

The 5'- and 3'-ends were generated by the RACE technique as disclosed above. The 5'-end obtained was a fragment of 988 bp (5PM; FIG. 9) that contained the first ATG codon and putative signal peptide. The 3'-end obtained was a cDNA fragment of 730 bp (3PM; FIG. 9) that contained a polyA tail. An overview of the cloning strategy is given in FIG. 9. All cDNA fragments were sequenced in full. The resulting nucleotide and deduced amino acid sequences are shown in FIG. 8. The identity of the clones with the isolated protein was verified by the partial amino acid sequences from the protein, as indicated by underlining in FIG. 8. The full-length cDNA encoded a total of 4175 bp with an open reading frame (ORF) starting with the first ATG codon at position 130 and ending with the TAA codon at position 3681 (SEQ ID NO: 1). The sequence flanking the first ATG codon conforms to the consensus sequence for initiation of translation proposed by Kozak (1991, supra), A/GXX-AUGG (SEQ ID NO:20). The ORF codes for a protein of 1184 amino acids, with a calculated molecular mass of 132,500. Prediction of the eukaryotic secretory signal sequence according to Von Heijne (1986) indicates that a putative cleavage site exists between amino acids 21 and 22. The protein contains 40 cysteine residues, which are likely to be involved in disulfide bond formation. Many of these are located towards the N-terminal part of the molecule. There are 8 consensus sites for N-glycosylation and the calculated isoelectric point is 8.31.

A 3' non-coding region of 493 bp downstream of the stop codon contains two consensus sequences for polyadenylation, 5'-AATAAA-3', at positions 4132–4137 and at 4140–4145 followed by a short poly-A stretch located 17 bp after the second polyadenylation signal (see FIG. 8 and SEQ ID NO: 1).

The mRNA for CILP was found to encode, in addition to CILP, a protein homologous to an ectonucleotide pyrophosphohydrolase recently cloned and partially sequenced from porcine chondrocytes (Masuda et al., 1997, "Molecular cloning and expression of a porcine chondrocyte nucleotide pyrophosphohydrolase", *Gene* 197:277–287).

Isolation and peptide mapping of CILP enabled the selection of probes and primers for characterization of the full length cDNA coding for the novel extracellular matrix macromolecule. This protein acts as a precursor for two different proteins. The cloning of a cDNA of 4175 bp that is transcribed to a single mRNA species of the same size, indicates that the mRNA encodes a larger protein than expected for CILP. This was verified by the complete deduced amino acid sequence. The polypeptide consists of 1184 amino acids with a calculated molecular mass of 132,500. Thus, the precursor protein is made of CILP (calculated molecular mass of 78,500, without post-translational modifications) and a protein homologous to a nucleotide pyrophosphohydrolase (NTPPHase) described in porcine chondrocytes (Masuda et al., 1997, supra). The proteolytic fragment of the porcine NTPPHase was suggested to be derived from a larger matrix vesicle-associated protein of apparent molecular weight 127 kDa (Masuda et al., 1995, "A unique ectonucleotide pyrophosphohydrolase associated with porcine chondrocytevesicles", *J. Clin. Invest.* 95:699–704). In this disclosure, the human homolog of the porcine NTPPHase has 460 amino acid residues with a molecular mass of 51,800, without posttranslational modifications. In the precursor protein described here, the two proteins appear to be generated after proteolytic cleavage at a tetrapeptide conforming to a furin proteinase cleavage consensus sequence RXK/RR (RNKR, spanning amino acids from 700 to 703 in FIG. 8) with basic amino acids in positions-4, -2 and -1 relative to the cleavage site (Hosaka et al., 1991, "Arg-X-Lys/Arg motif as a signal for precursor cleavage catalyzed by furin within the constitutive secretory pathway", *J. Biol. Chem.* 266: 12127–121 30). This motif is conserved in a number of constitutively processed precursors. Whether the presently described precursor protein is cleaved by furin or furin-like proteases synthesized by human chondrocytes remains to be established.

The precursor protein is synthesized as a single polypeptide chain as shown by in vitro expression. The precursor protein is cleaved to two proteins in the cell systems used for in vivo expression. One protein is the CILP: the other protein is a protein homologous to murine NTPPHase. The presence of small amounts of the cleaved products in the COS-7 cell extract upon transient expression indicates that the cleavage occurs intracellularly, probably immediately prior to secretion. Both products, CILP and the homologous NTPPHase, are fully secreted from the cells as shown in the two cell systems used for the study of the expression of the protein. Only in the COS-7 cells is a proportion of the precursor protein secreted into the medium, possibly a result from a limited capacity to process the high-level of protein expressed in these cells after transfection.

More complete processing was accomplished in the EBNA cells, where the proform of the protein was not secreted into the medium. After processing, a product corresponding to CILP isolated from human articular cartilage (92 kDa) and its smaller variant (82 kDa) were detected by a polyclonal antibody against CILP. The smaller product might be formed by an alternative cleavage site used by the proteases in the expression system. Since this smaller form is not detected in explants of human articular cartilage, it either has a faster turnover or the processing enzymes in human articular chondrocytes are more specific than those in the EBNA cells. Alternative putative cleavage site spanning amino acids 518–519 or 531–535 (FIG. 8; SEQ ID NO:2) might be targeted in the cell lines used.

CILP is processed by the cells into a single polypeptide chain with a calculated molecular mass of 78,500. It is slightly basic with an isoelectric point of 8.15. It contains 6 putative glycosylation sites, which is consistent with a molecular mass of 92,000, the apparent molecular mass of the protein purified from human articular cartilage after post-translational modifications. The protein contains 30 cysteine residues mostly distributed towards the N-terminal half of the molecule. Due to the special role of cysteine residues for protein structure, the high content of these amino acids indicates a high degree of intrachain disulfide cross-bridging.

Towards the N-terminus of the molecule, there is a stretch of 27 amino acids, from 131 to 157, shown in FIG. 8 (SEQ ID NO:2), which is related to the Type I repeats of thrombospondin (Lawler and Hynes, 1986, "The structure of human thrombospondin, an adhesive glycoprotein with multiple calcium binding sites and homologies with several different proteins", *J. Cell Biol.* 103:1635–1648). The N-terminal domain of CILP containing the Type I thrombospondin-like repeat and 16 cysteines is associated with a strikingly hydrophobic region from amino acids 130–225. Following this, a relatively exposed region might lead to another compact, disulfide bonded region between residues 354–445. Another extended region with no cysteines leads to the very basic furin-type cleavage site.

The C-terminal portion of the molecule shows very high similarity to a porcine ectonucleotide pyrophosphohydrolase, NTPPHase (Masuda et al., 1997, supra). The human homolog of the nucleotide pyrophosphohydrolase (NTPPHase) that forms the C-terminal of CILP is made of 460 amino acid residues, with a calculated molecular mass of 51,800, and an isoelectric point 8.73. It has 10 cysteine residues and two putative N-glycosylation sites. This is in close agreement with the molecular mass estimate for the catalytically active fragment of the porcine NTPPHase (Masuda et al., 1995, supra).

Based on the biochemical characterization of CILP, which has an apparent molecular mass of 92,000, and on the N-terminal sequence reported for a catalytically active proteolytic fragment of the porcine NTPPHase (Masuda et al., 1995, supra), it appears that CILP is synthesized as a proform that also contains a protein homologous to a porcine enzyme with NTPPHase activity. In fact the precursor protein has a consensus sequence for precursor cleavage catalyzed by furin (Hosaka et al., 1991, supra), i.e., RXK/RR from positions 700 to 703 (RNKR). Directly following the furin consensus cleavage site is the start of the region with homology to the N-terminus of the NTPPHase. The proteolytic fragment of the porcine enzyme has a molecular mass of 61,000, which is in agreement with the calculated molecular mass of 51,800 of the translated sequence from base 2302 to base 3684, assuming carbohydrate substitutions at two putative N-glycosylation sites.

The lack of similarities between CILP and other proteins of defined structure did not allow prediction of a secondary structure or any remarkable structural feature or function. The Type I repeat structure is similar to that of the consensus sequence for heparin binding (Guo et al., 1992, "Heparin-binding peptides from the type I repeats of thrombospondin: Structural requirements for heparin binding and promotion of melanoma cell adhesion and chemotaxis", *J. Biol. Chem.* 267:19349–19355), from residues 131 to 135 (WSPWS; SEQ ID NO:21), but no experimental evidence that CILP actually binds to heparin has yet been obtained.

Example 10

Northern Blotting

Ten micrograms of total RNA isolated from human articular cartilage were electrophoresed on a 1% formaldehyde-agarose gel, nitrocellulose filter (NitroPure, Micron Separation) and hybridized with random-primed [$\alpha$-$^{32}$P]dCTP probe of 1585-bp BsmI/EcoRI fragment from the 92C-1 clone. After hybridization, the membrane was washed twice at 42° C. for 15 minutes with 2× SSC, 0.1% SDS, then with 1× SSC, 0.1% SDS, and finally with 0.1× SSC, 0.1% SDS, and exposed to X-ray film (X-OMAT-AR, Kodak).

Northern blotting of total RNA from human articular cartilage, using a 1585 bp BsmI/EcoRI fragment from clone 92C-I as the probe, indicated that there is a single mRNA of approximately 4.2 kb (FIG. 10). This size agrees well with the total number of nucleotides sequenced, indicating that most of the mRNA is covered by the cDNA clones.

Example 11

Expression Constructs

A full length cDNA for expression studies in three vectors was constructed as schematically depicted in FIG. 9.

In pBluescript II KS(+) (Stratagene) the clone 92C-2 was digested with XhoI, blunt ended with T4 DNA polymerase, extracted with phenol, and then digested with AvrII. The released fragment (1081 bp) was separated by agarose electrophoresis, isolated, and ligated into the clone 92C-1, previously digested with SmaI/AvrII. The insert was then released with XhoI and ligated into another pBluescript II KS(+) containing a 606 bp XhoI/EcoRI fragment of the human CILP gene containing the 3' end. The use of this genomic fragment (606 bp) was for convenience. It did not contain an intron and its sequence was identical to the 3MC clone except for the polyA tail. The 5' end was amplified by PCR using the 5'Marathon Clone (5PM) as a template. A synthetic forward primer was used, specific for the region surrounding position 97, and with a ClaI site introduced. A synthetic reverse primer was used, specific for the region surrounding position 843, near the SauI site of the template. The PCR product was 746 bp. It was ligated in the recombinant clone.

To make a construct in the pSVL SV40 Late Promoter Expression Vector (Pharmacia Biotech), pBluescript II KS(+) bearing the full length CILP cDNA was digested with SalI/SacI. The PCR fragment described above was ligated into the pSVL SV40 vector, which had previously been digested with XhoI/SacI. The 746 bp ClaI/SauI fragment was then added. In pCEP 4 (Invitrogen), the full length CILP cDNA was ligated into the NotI/KpnI site. All three vectors containing full length CILP cDNA were checked by standard sequencing with forward and reverse primers that covered the ligation sites.

Example 12

CILP Expression and Detection Using In Vitro Transcription/Translation Assays

Figures 11A, 11B, 11C:
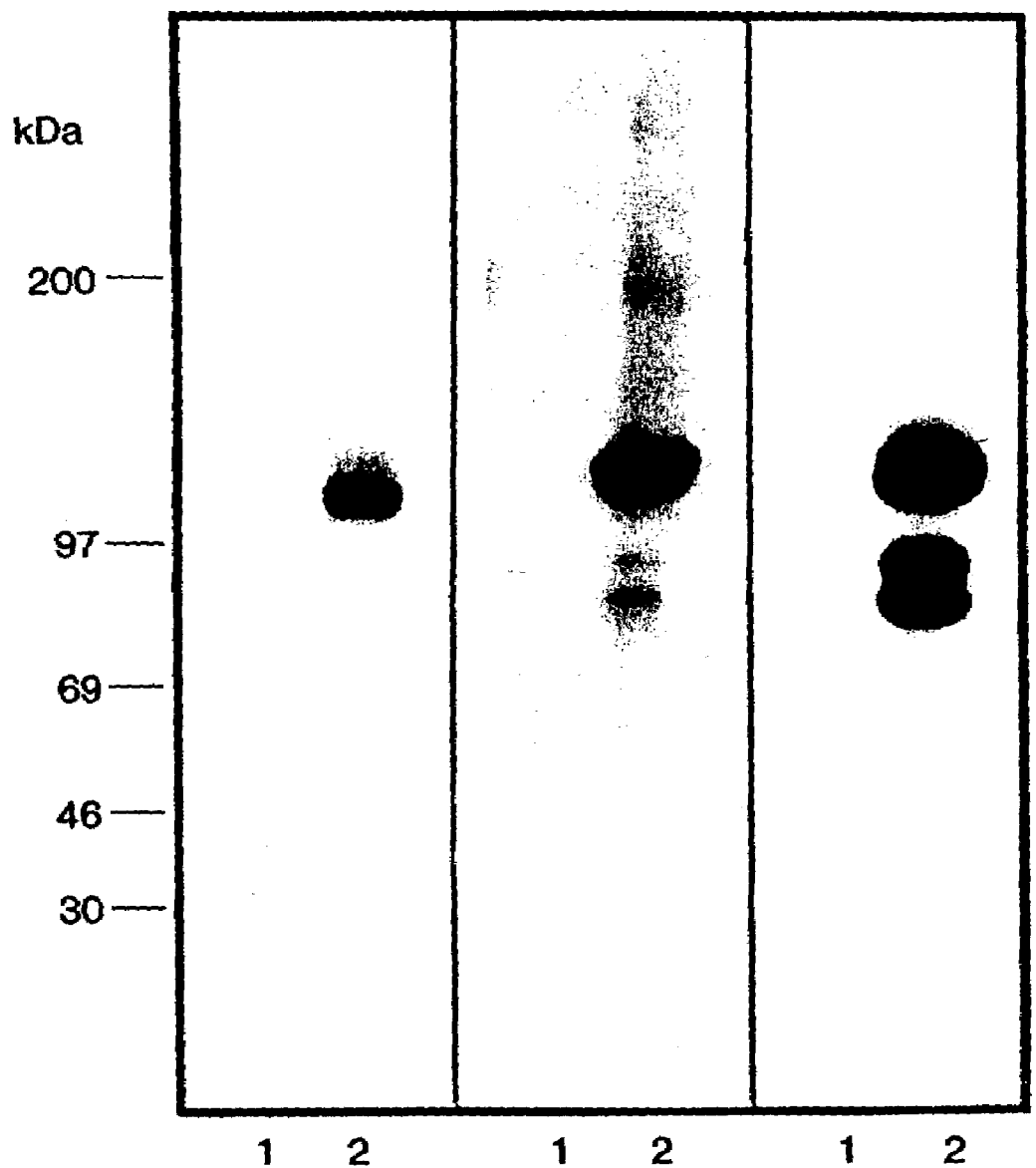

The plasmid pBluescript II KS(+) with the expression construct (FIG. 9) was transcribed/translated in vitro with TNT® T 3 Polymerase (TNT®T3 Coupled Reticulocyte Lysate System, Promega). Supercoiled plasmid (500 ng), was used according to the manufacturer's protocol. The 25 µl reaction mixture contained 12.5 µl of TNT rabbit reticulocyte lysate, TNT reaction buffer, T3 RNA polymerase, RNasin® 20 Units, and amino acid mix without methionine, supplemented with [$^{35}$S]methionine as the radioactive precursor (1000 Ci/mmol). After 90 minutes of incubation at 30° C., labeled polypeptides were separated from free amino acids by ethanol precipitation (10 volumes of ethanol containing 50 mM sodium acetate). Precipitates were resuspended in electrophoresis sample buffer (2% SDS, 0.125 M Tris-HCl, pH 6.8, 0.002% Bromophenol blue, and 20% Glycerol) with or without 10% 2-mercaptoethanol. The resuspended precipitates were boiled at 100° C. for 4 minutes, electrophoresed on 4–16% gradient SDS-polyacrylamide gels according to Laemmli (1970, supra), and visualized by fluorography (Chamberlain, 1979, "Fluorographic detection of radioactivity in polyacrylamide gels with the water-soluble fluor, sodium salicylate", *Anal. Biochem.* 98:132–135). A control reaction with the pBluescript II KS(+) plasmid only was run simultaneously. In vitro expression using the cell-free transcription-translation system in the presence of [$^{35}$S]methionine resulted in detection of a single labeled peptide with an apparent molecular mass of 123,000 (FIG. 11A).

Example 13

CILP Expression and Detection in Vivo

The processing of the precursor protein was studied by expressing the cDNA construct transiently and stably in two different cell lines.

Transient Transfection

The monkey kidney-derived cell line, COS-7, was grown in F12 Dulbecco's medium, supplemented with 10% fetal calf serum, streptomycin (0.1 mg/mil), and penicillin (100 units/ml) at 37° C. in a $CO_2$ incubator. Semi-confluent cells were transfected using the lipofectamine method, as described by the manufacturer (Life Technologies, Inc.), with either 6 µg of pSVL SV40 vector containing the expression construct or 6 µg of pSVL SV40 vector only. After 72 hours (post transfection) the cells were labeled with [$^{35}$S]methionine (1000 Ci/mmol) in a methionine-free medium. After 8 hours of labeling, the medium was removed, the cells were washed with PBS, and the cells were lysed with RIPA buffer (0.5% of NP 40, 0.5% Tween 20, 0.5% deoxycholic acid, 0.15 M NaCl, 10 mM KCl, 1 mM EDTA, and 20 mM Tris-HCl, pH7). The medium and the cell extract were independently immunoprecipitated with polyclonal rabbit antiserum raised against CILP. The precipitated products were electrophoresed on a 4–16% gradient SDS-polyacrylamide gel and visualized by fluorography. As a control, the cells were transfected with the respective vector lacking the cDNA insert.

With COS-7 cells, analysis by immunoprecipitation of cell extracts and medium with polyclonal antibodies against CILP showed that the precursor protein was secreted to the medium in three forms (FIGS. 11B and 11C). One component had an apparent molecular weight slightly larger (i.e., 138 kDa) than the in vitro translated product, and probably represents the precursor protein with post-translational modifications. Two smaller components had apparent molecular weights of 92 and 82 kDa, respectively. The 92 kDa component is the same size as the expected size for CILP. In the cell extract the major component was the higher molecular weight product (138 kDa, FIG. 11B), even though small amounts of the two components of lower molecular weight could be seen (92 and 82 kDa, respectively).

Stable Transfections

Human embryonic kidney cells, 293-EBNA, (Invitrogen) were grown in DMEM (Dulbecco's Modified Eagle's Medium) supplemented with 10% fetal calf serum, streptomycin (0.1 mg/ml), penicillin (100 units/ml), and 250 µg/ml Geneticin. When the cells were semi-confluent they were stably transfected using the lipofectamine method with either 5 µg of the pCEP4 vector containing the expression construct or 5 µg of the pCEP4 vector only. The cells were selected with 300 µg/ml hygromycin. After one week of transfection the expression of CILP was analyzed by immunoblotting the medium.

Figures 12A, 12B:
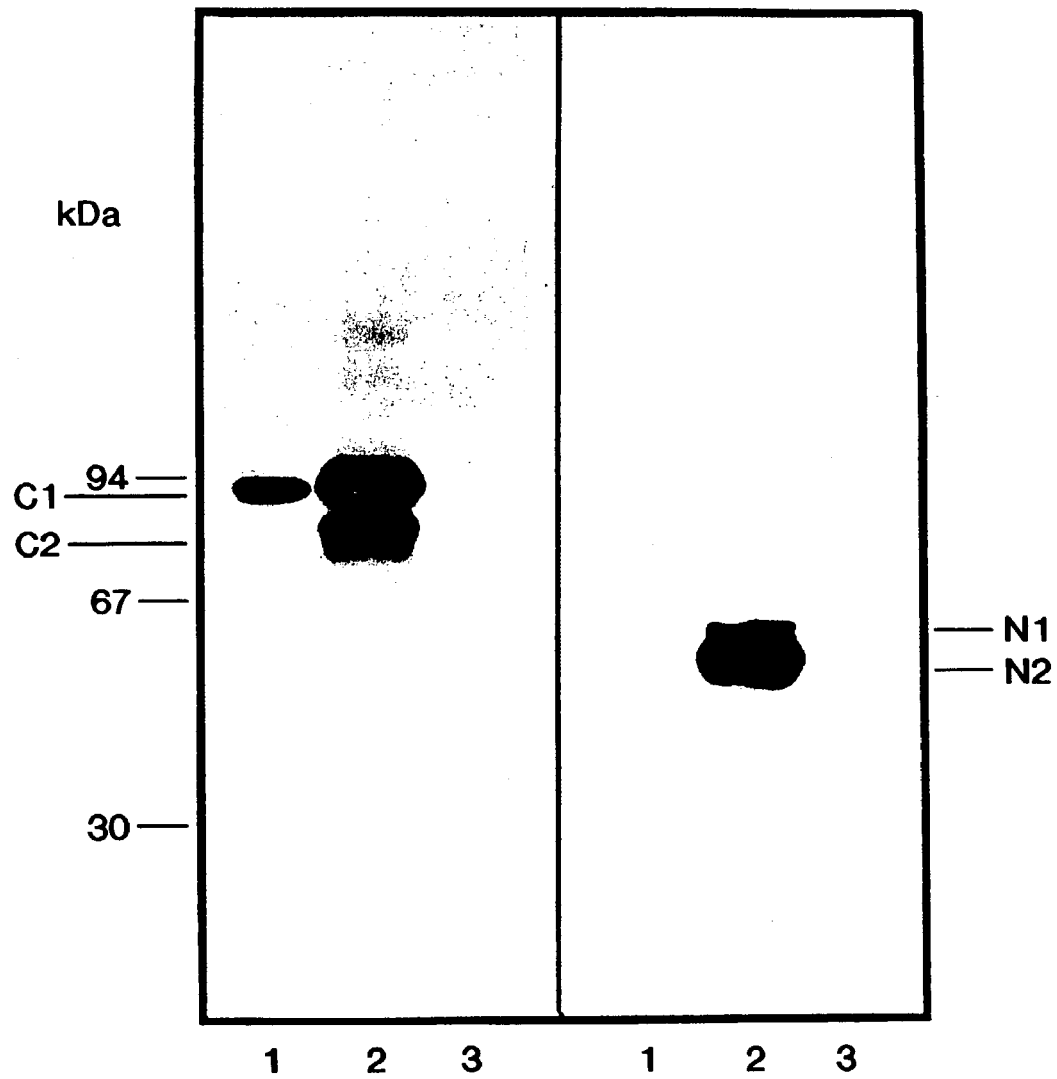

The processing of the precursor protein was further analyzed by immunoblotting of the medium from 293-EBNA cells after stable transfection and expression (FIG. 12). Polyclonal antibodies against CILP recognized a major component with a molecular mass corresponding to isolated CILP, C1 (FIG. 12A). An additional immunoreactive component of lower molecular weight (i.e., C2, 82 kDa) was present in a lower proportion (FIG. 12A). This lower molecular weight component is not a result of different glycosylation of CILP since after digestion with N-glycanase both proteins showed a similar change in their electrophoretic mobility (data not shown).

It is likely then that this form is generated by alternative cleavage of the precursor protein. With antibodies generated against the synthetic peptide EDRTFLVGNLEIRERRLFC (SEQ ID NO:22; FIG. 12B), corresponding to the N-terminus of NTPPHase region, a major component with a molecular mass about 60,000 (N2, FIG. 12B) was detected. An additional minor component with slightly lower mobility (N1, FIG. 12B) was recognized by the antibody. The apparent molecular mass of the major band (60,000; N2) corresponds with that reported for a proteolytic fragment of the porcine NTPPHase (Masuda et al., 1995, supra). The presence of these two forms of CILP as well as the putative NTPPHase, differing in size, suggests an alternative cleavage site of the precursor protein. There are basic di- and tri-peptides, between residues 518–519, and 531–535 (FIG. 8; SEQ ID NO:2) that might represent cleavage sites for furin-like proteinases. These sites are 164 and 150 amino acids upstream of the furin proteinase cleavage consensus sequence. Cleavage at either of these sites would alter the molecular weight by 16.4 and 15 kDa, respectively. These values correspond well to the difference in apparent molecular weight between the observed CILP forms as well as the NTPPHase forms detected by the respective antibodies, i.e., 92 kDa vs. 82 kDa for CILP. In summary, these experiments show that the precursor protein is fully cleaved by the 293-EBNA cells into two components that are secreted to the medium with no detectable precursor present.

It will be apparent to those skilled in the art that various modifications and variations can be made in the practice of the present invention without departing from the scope or spirit of the invention. Other embodiments of the invention will be apparent to those skilled in the art from consideration of the specification and practice of the invention disclosed herein. All references cited herein are incorporated in their entirety by reference.

What is claimed is:

1. An isolated or purified cartilage intermediate layer protein (CILP), wherein said CILP consists of residues 1–703 of SEQ ID NO:2 and has a molecular mass of 92,000 when expressed in a cell.

2. An isolated or purified cartilage intermediate layer protein (CILP), wherein said CILP is produced by expressing a nucleic acid comprising the sequence of SEQ ID NO:1 in a host cell and permitting the host cell to cleave the polypeptide encoded by said nucleic acid into said CILP and a nucleotide pyrophosphohydrolase, wherein said CILP has a molecular mass of 92,000 after processing by the cell.

3. An isolated or purified cartilage intermediate layer protein (CILP) encoded by SEQ ID NO:1.

4. An isolated or purified peptide consisting of residues 1–703 of SEQ ID NO:2.

5. The peptide of claim 4, wherein the peptide is a mammalian peptide.

6. The peptide of claim 4, wherein the peptide is a human peptide.

7. The peptide of claim 4, wherein the peptide is a recombinant peptide.

8. The peptide of claim 4, wherein the peptide is isolated from chondrocyte-containing tissues.

9. The peptide of claim 4, wherein the peptide is expressed in early osteoarthritis.

* * * * *

UNITED STATES PATENT AND TRADEMARK OFFICE
CERTIFICATE OF CORRECTION

PATENT NO. : 7,211,649 B1  Page 1 of 1
APPLICATION NO. : 10/349188
DATED : May 1, 2007
INVENTOR(S) : Dick Heinegård and Pilar Lorenzo It is certified that error appears in the above-identified patent and that said Letters Patent is hereby corrected as shown below:

Title page, item (75), "Dick Heinegard" should read
--Dick Heinegård--.

Title page, item (73), "Ana Mar Medical AB" should read
--AnaMar Medical AB--.

Signed and Sealed this

Twenty-sixth Day of June, 2007

JON W. DUDAS
*Director of the United States Patent and Trademark Office*